(12) United States Patent
Kim et al.

(10) Patent No.: US 11,877,512 B2
(45) Date of Patent: Jan. 16, 2024

(54) ORGANIC ELECTROLUMINESCENCE DEVICE AND COMPOUND FOR ORGANIC ELECTROLUMINESCENCE DEVICE

(71) Applicants: Samsung Display Co., Ltd., Yongin-si (KR); Lapto Co., Ltd., Seongnam-si (KR)

(72) Inventors: SeulOng Kim, Hwaseong-si (KR); Eu Gene Oh, Seoul (KR); Hyein Jeong, Suwon-si (KR); Seung-Jin Chu, Gwangmyeong-si (KR); Munsoo Kim, Seongnam-si (KR); Juwan Maeng, Seongnam-si (KR); Kap Jong Han, Gwangju-si (KR)

(73) Assignees: Samsung Display Co., Ltd., Yongin-si (KR); Lapto Co., Ltd., Seongnam-si (KR)

( * ) Notice: Subject to any disclaimer, the term of this patent is extended or adjusted under 35 U.S.C. 154(b) by 665 days.

(21) Appl. No.: 17/028,938

(22) Filed: Sep. 22, 2020

(65) Prior Publication Data

US 2021/0098708 A1    Apr. 1, 2021

(30) Foreign Application Priority Data

Sep. 30, 2019   (KR) .................. 10-2019-0121047

(51) Int. Cl.
| | |
|---|---|
| *H10K 85/60* | (2023.01) |
| *H10K 85/30* | (2023.01) |
| *H10K 50/12* | (2023.01) |
| *C09K 11/06* | (2006.01) |
| *C07D 519/00* | (2006.01) |
| *C07F 5/02* | (2006.01) |
| *C07D 498/04* | (2006.01) |

(52) U.S. Cl.
CPC ......... *H10K 85/656* (2023.02); *C07D 498/04* (2013.01); *C07D 519/00* (2013.01); *C07F 5/027* (2013.01); *C09K 11/06* (2013.01); *H10K 85/324* (2023.02); *H10K 85/636* (2023.02); *H10K 85/654* (2023.02); *C09K 2211/1033* (2013.01); *H10K 50/12* (2023.02)

(58) Field of Classification Search
None
See application file for complete search history.

(56) References Cited

U.S. PATENT DOCUMENTS

| | | | |
|---|---|---|---|
| 9,136,481 | B2 | 9/2015 | Kang et al. |
| 9,793,492 | B2 | 10/2017 | Sagara et al. |
| 2015/0239880 | A1 | 8/2015 | Adachi et al. |
| 2021/0098701 | A1 | 4/2021 | Lee et al. |
| 2021/0098711 | A1 | 4/2021 | Lee et al. |
| 2021/0098715 | A1 | 4/2021 | Kim et al. |

FOREIGN PATENT DOCUMENTS

| | | | | |
|---|---|---|---|---|
| KR | 10-1117621 | B1 | | 3/2012 |
| KR | 10-1297158 | B1 | | 8/2013 |
| KR | 10-2015-0050570 | A | | 5/2015 |
| KR | 2020100972 | A | * | 8/2020 ............. C09K 11/06 |
| KR | 1020210038783 | A | | 4/2021 |
| KR | 1020210038788 | A | | 4/2021 |
| KR | 1020210038789 | A | | 4/2021 |

OTHER PUBLICATIONS

KR20200100972 English Machine Translation, prepared May 20, 2023. (Year: 2023).*

* cited by examiner

*Primary Examiner* — Christopher M Rodd
(74) *Attorney, Agent, or Firm* — Lewis Roca Rothgerber Christie LLP

(57) ABSTRACT

An organic electroluminescence device of an embodiment includes a first electrode, a second electrode, and an emission layer between the first electrode and the second electrode, wherein the emission layer includes a compound represented by Formula 1, thereby showing excellent emission efficiency properties and long-life characteristics:

Formula 1

16 Claims, 2 Drawing Sheets

ORGANIC ELECTROLUMINESCENCE DEVICE AND COMPOUND FOR ORGANIC ELECTROLUMINESCENCE DEVICE

CROSS-REFERENCE TO RELATED APPLICATIONS

This application claims priority to and the benefit of Korean Patent Application No. 10-2019-0121047, filed on Sep. 30, 2019, the entire content of which is hereby incorporated by reference.

BACKGROUND

One or more aspects of embodiments of the present disclosure herein relate to an organic electroluminescence device and a compound used therein, and more particularly, to a compound used as a light-emitting material and an organic electroluminescence device including the same.

Recently, the development of an organic electroluminescence display as an image display is being actively conducted. Different from a liquid crystal display, the organic electroluminescence display is a self-luminescent display in which holes and electrons respectively injected from a first electrode and a second electrode recombine in an emission layer, and a light-emitting material including an organic compound in the emission layer emits light to attain display of images.

In the application of an organic electroluminescence device to a display, the decrease of the driving voltage, and the increase of the emission efficiency and the life of the organic electroluminescence device are required (or desired), and developments on materials for an organic electroluminescence device capable of stably (or suitably) attaining these characteristics are being continuously sought.

Particularly, recently, in order to accomplish an organic electroluminescence device with high efficiency, techniques on phosphorescence emission, which uses energy in a triplet state, or delayed fluorescence emission, which uses the generating phenomenon of singlet excitons by the collision of triplet excitons (triplet-triplet annihilation, TTA), are being developed, and development of a material for thermally activated delayed fluorescence (TADF) using delayed fluorescence phenomenon is being conducted.

SUMMARY

One or more aspects of embodiments of the present disclosure are directed toward an organic electroluminescence device showing excellent (or improved) emission efficiency and long-life characteristics.

One or more aspects of embodiments of the present disclosure are also directed toward a compound that is a material for an organic electroluminescence device having excellent (or improved) emission efficiency and long-life characteristics.

According to an embodiment, there is provided a compound represented by the following Formula 1:

Formula 1

In Formula 1, $X_1$ to $X_4$ may each independently be $CR_a$, L may be a substituted or unsubstituted arylene group of 6 to 30 carbon atoms for forming a ring, or a substituted or unsubstituted heteroarylene group of 2 to 30 carbon atoms for forming a ring, and "n" may be 1 or 2. Ar may be a substituted or unsubstituted hydrocarbon ring group of 6 to 30 carbon atoms for forming a ring, or a substituted or unsubstituted heterocyclic group of 2 to 30 carbon atoms for forming a ring, and $R_a$ may be a hydrogen atom, a deuterium atom, a halogen atom, a cyano group, a substituted or unsubstituted silyl group, a substituted or unsubstituted amine group, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, and/or combined with an adjacent group to form a ring.

In an embodiment, Formula 1 may be represented by the following Formula 1-1:

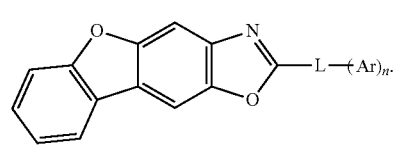

Formula 1-1

In Formula 1-1, L, "n", and Ar are the same as defined in Formula 1.

In an embodiment, Ar may be an unsubstituted aryl group of 6 to 20 carbon atoms for forming a ring, or a substituted or unsubstituted heteroaryl group of 2 to 20 carbon atoms for forming a ring, the heteroaryl group including at least one selected from N, O and B as a ring-forming atom.

In an embodiment, Ar may be represented by the following Formula 2:

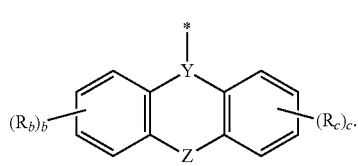

Formula 2

In Formula 2, Y may be N or B, Z may be a direct linkage, O, S, $NR_d$, or $CR_eR_f$, and "b" and "c" may each independently be an integer of 0 to 4. $R_b$ to $R_f$ may each independently be a hydrogen atom, a deuterium atom, a halogen atom, a cyano group, a substituted or unsubstituted silyl group, a substituted or unsubstituted amine group, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, and/or combined with an adjacent group to form a ring.

In an embodiment, Formula 2 may be represented by the following Formula 2-1 or Formula 2-2:

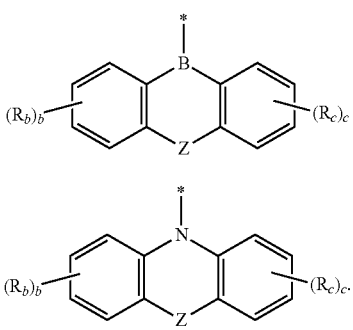

Formula 2-1

Formula 2-2

In Formula 2-1 and Formula 2-2, Z, $R_b$, $R_c$, "b", and "c" are the same as defined in Formula 2.

In an embodiment, Formula 2-2 may be represented by any one among the following Formula 2-2A to Formula 2-2E:

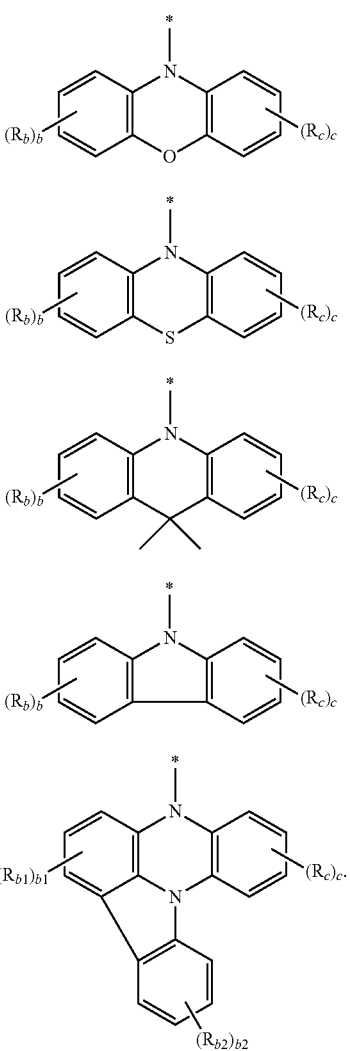

Formula 2-2A

Formula 2-2B

Formula 2-2C

Formula 2-2D

Formula 2-2E

In Formula 2-2E, "b1" may be an integer of 0 to 3, "b2" may be an integer of 0 to 4, and $R_{b1}$ and $R_{b2}$ may each independently be a hydrogen atom, a deuterium atom, a halogen atom, a cyano group, a substituted or unsubstituted silyl group, a substituted or unsubstituted amine group, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, and/or combined with an adjacent group to form a ring. In Formula 2-2A to Formula 2-2E, $R_b$, $R_c$, "b", and "c" are the same as defined in Formula 2.

In an embodiment, the compound represented by Formula 1 may be a green dopant emitting green light having a central wavelength of about 500 nm to about 550 nm.

In an embodiment, the compound represented by Formula 1 may be a blue dopant emitting blue light having a central wavelength of about 420 nm to about 470 nm.

In an embodiment, the compound represented by Formula 1 may have an absolute value ($\Delta E_{ST}$) of a difference between the lowest excitation singlet energy level (S1) and the lowest excitation triplet energy level (T1) of about 0.2 eV or less.

According to an embodiment of the present disclosure, there is provided an organic electroluminescence device including a first electrode; a second electrode on the first electrode; and an emission layer between the first electrode and the second electrode and including the aforementioned compound of an embodiment. In the compound, L may be a substituted or unsubstituted phenylene group, or a substituted or unsubstituted pyridylene group.

In an embodiment, the emission layer may include a host and a dopant, and the host may include the compound of an embodiment.

In an embodiment, the emission layer may be to emit delayed fluorescence, and the compound may be a delayed fluorescence dopant.

In an embodiment, the emission layer may be to emit light having a central wavelength of about 500 nm to about 550 nm, or light having a central wavelength of about 420 nm to about 470 nm.

BRIEF DESCRIPTION OF THE FIGURES

The accompanying drawings are included to provide a further understanding of the present disclosure and are incorporated in and constitute a part of this specification. The drawings illustrate example embodiments of the present disclosure and, together with the description, serve to explain principles of the present disclosure. In the drawings.

DETAILED DESCRIPTION

Figure 1:
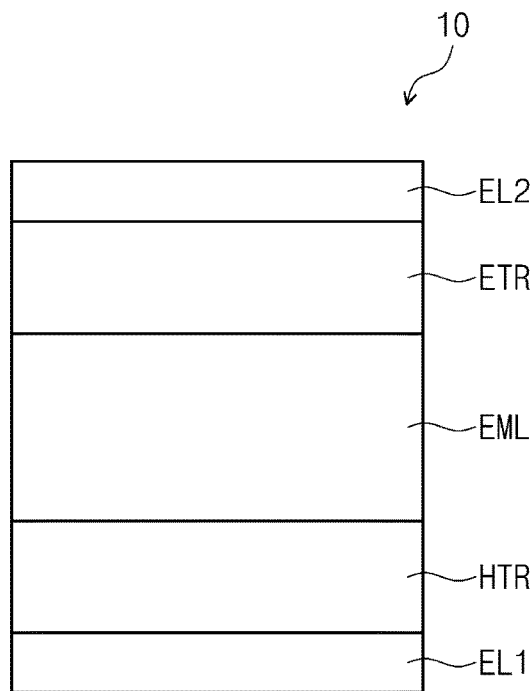
FIG. 1 is a cross-sectional view schematically illustrating an organic electroluminescence device according to an embodiment of the present disclosure.

The present disclosure may have various modifications and may be embodied in different forms, and example embodiments will be explained in more detail with reference to the accompany drawings. The present disclosure may, however, be embodied in different forms and should not be construed as limited to the embodiments set forth herein.

Rather, all modifications, equivalents, and substituents which are included in the spirit and technical scope of the present disclosure should be included in the present disclosure.

It will be understood that when an element (or region, layer, part, etc.) is referred to as being "on", "connected to" or "coupled to" another element, it can be directly on, connected or coupled to the other element (without any intervening elements therebetween), or one or more third intervening element(s) may be present.

Like reference numerals refer to like elements throughout the specification and drawings. In addition, in the drawings, the thickness, the ratio, and the dimensions of constituent elements are exaggerated for effective explanation of technical contents.

The term "and/or" includes one or more combinations which may be defined by relevant elements. Expressions such as "at least one of," "one of," and "selected from," when preceding a list of elements, modify the entire list of elements and do not modify the individual elements of the list. Further, the use of "may" when describing embodiments of the present disclosure refers to "one or more embodiments of the present disclosure."

It will be understood that, although the terms first, second, etc. may be used herein to describe various elements, these elements should not be limited by these terms. These terms are only used to distinguish one element from another element. Thus, a first element could be termed a second element without departing from the teachings of the present invention. Similarly, a second element could be termed a first element. As used herein, the singular forms are intended to include the plural forms as well, unless the context clearly indicates otherwise.

In addition, the terms "below", "beneath", "on" and "above" are used for explaining the relation of elements shown in the drawings. These terms refer to relative concepts and are to be interpreted based on the direction shown in the drawing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It will be further understood that the terms "comprises" and/or "comprising," when used in this specification, specify the presence of stated features, numerals, steps, acts, operations, elements, parts, or the combination thereof, but do not preclude the presence or addition of one or more other features, numerals, steps, acts, operations, elements, parts, or the combination thereof.

Hereinafter, the organic electroluminescence device according to an embodiment of the present disclosure and a compound of an embodiment, included therein will be explained with reference to attached drawings.

FIG. 1 to FIG. 4 are cross-sectional views schematically showing organic electroluminescence devices according to example embodiments of the present disclosure. Referring to FIG. 1 to FIG. 4, in an organic electroluminescence device 10 of an embodiment, a first electrode EL1 and a second electrode EL2 are oppositely positioned, and between the first electrode EL1 and the second electrode EL2, an emission layer EML may be provided.

In addition, the organic electroluminescence device 10 of an embodiment further includes a plurality of functional layers between the first electrode EL1 and the second electrode EL2, in addition to the emission layer EML. The plurality of the functional layers may include a hole transport region HTR and an electron transport region ETR. For example, the organic electroluminescence device 10 according to an embodiment may include a first electrode EL1, a hole transport region HTR, an emission layer EML, an electron transport region ETR, and a second electrode EL2, stacked in this order. In addition, the organic electroluminescence device 10 of an embodiment may include a capping layer CPL on the second electrode EL2.

The organic electroluminescence device 10 of an embodiment may include a compound of an embodiment, which will be explained in more detail herein below, in the emission layer EML, which is positioned between the first electrode EL1 and the second electrode EL2. However, an embodiment of the present disclosure is not limited thereto, and the organic electroluminescence device 10 of an embodiment may include the compound according to an embodiment in a hole transport region HTR or an electron transport region ETR, which are included in the plurality of functional layers between the first electrode EL1 and the second electrode EL2.

Figure 2:
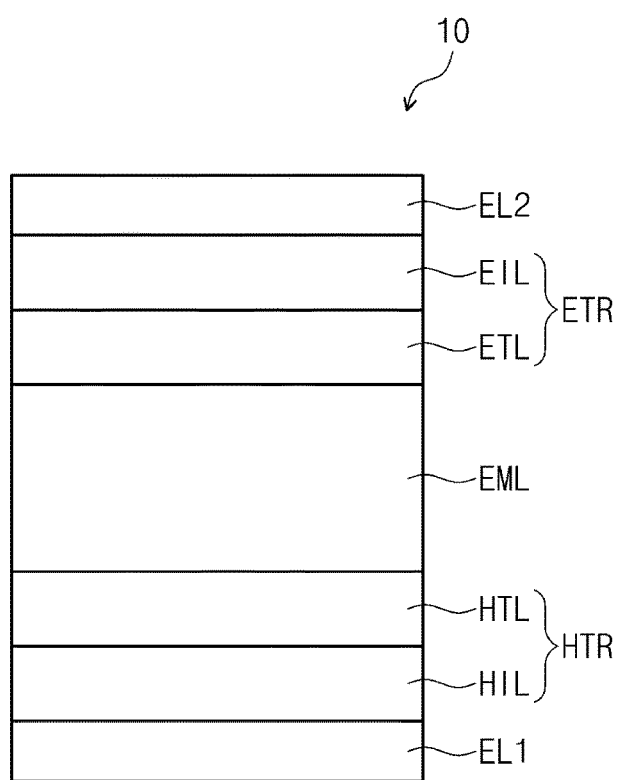
FIG. 2 is a cross-sectional view schematically illustrating an organic electroluminescence device according to an embodiment of the present disclosure.
Figure 3:
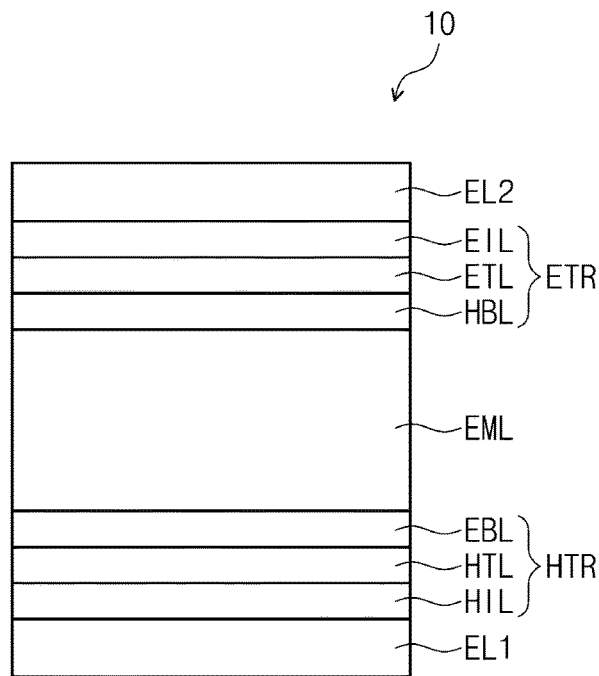
FIG. 3 is a cross-sectional view schematically illustrating an organic electroluminescence device according to an embodiment of the present disclosure.
Figure 4:
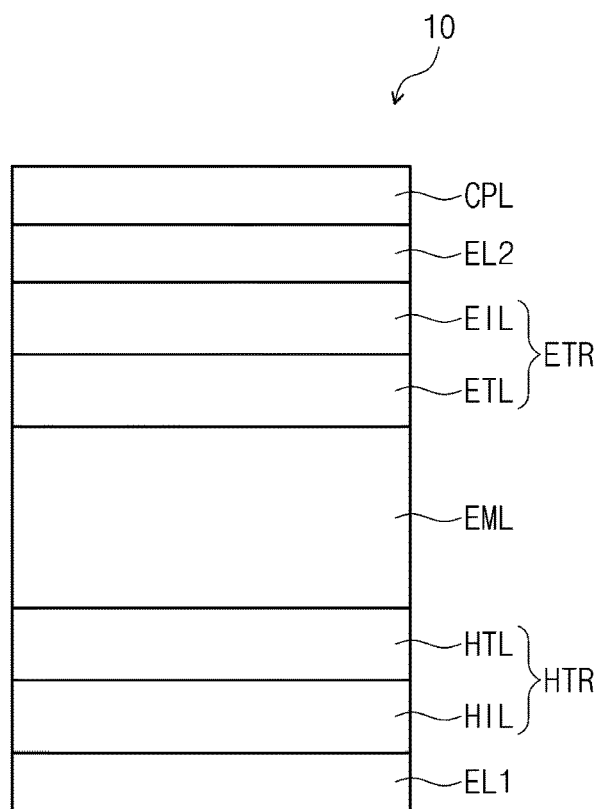
FIG. 4 is a cross-sectional view schematically illustrating an organic electroluminescence device according to an embodiment of the present disclosure.

Meanwhile, when compared with FIG. 1, FIG. 2 shows the cross-sectional view of an organic electroluminescence device 10 of an embodiment, wherein a hole transport region HTR includes a hole injection layer HIL and a hole transport layer HTL, and an electron transport region ETR includes an electron injection layer EIL and an electron transport layer ETL. In addition, when compared with FIG. 1, FIG. 3 shows the cross-sectional view of an organic electroluminescence device 10 of an embodiment, wherein a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL. When compared with FIG. 2, FIG. 4 shows the cross-sectional view of an organic electroluminescence device 10 of an embodiment, including a capping layer CPL on a second electrode EL2.

The first electrode EL1 has conductivity. The first electrode EU may be formed using a metal alloy or any suitable conductive compound. The first electrode EL1 may be an anode. In some embodiments, the first electrode EL1 may be a pixel electrode. The first electrode EL1 may be a transmissive electrode, a transflective electrode, or a reflective electrode. If the first electrode EL1 is the transmissive electrode, the first electrode EL1 may include a transparent metal oxide such as indium tin oxide (ITO), indium zinc oxide (IZO), zinc oxide (ZnO), and/or indium tin zinc oxide (ITZO). If the first electrode EU is the transflective electrode or the reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). In some embodiments, the first electrode EL1 may have a structure including a plurality of layers including a reflective layer or a transflective layer formed using any of the above materials, and a transmissive conductive layer formed using ITO, IZO, ZnO, and/or ITZO. For example, the first electrode EL1 may include a three-layer structure of ITO/Ag/ITO. However, an embodiment of the present disclosure is not limited thereto. The thickness of the first electrode EU may be from about 1,000 Å to about 10,000 Å, for example, from about 1,000 Å to about 3,000 Å.

The hole transport region HTR may be provided on the first electrode EL1. The hole transport region HTR may include at least one of a hole injection layer HIL, a hole transport layer HTL, a hole buffer layer, or an electron blocking layer EBL. The thickness of the hole transport region HTR may be from about 50 Å to about 15,000 Å.

The hole transport region HTR may have a single layer formed using a single material, a single layer formed using a plurality of different materials, or a multilayer structure including a plurality of layers formed using a plurality of different materials.

For example, the hole transport region HTR may have the structure of a single layer of a hole injection layer HIL, or a hole transport layer HTL, and may have a structure of a single layer formed using a hole injection material and a hole transport material. In some embodiments, the hole transport region HTR may have a structure of a single layer formed using a plurality of different materials, or a structure stacked from the first electrode EL1 of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer EBL, without limitation.

The hole transport region HTR may be formed using one or more suitable methods such as a vacuum deposition method, a spin coating method, a cast method, a Langmuir-Blodgett (LB) method, an inkjet printing method, a laser printing method, and/or a laser induced thermal imaging (LITI) method.

The hole injection layer HIL may include, for example, a phthalocyanine compound (such as copper phthalocyanine), $N^1,N^{1'}$-([1,1'-biphenyl]-4,4'-diyl)bis($N^1$-phenyl-$N^4,N^4$-di-m-tolylbenzene-1,4-diamine) (DNTPD), 4,4',4"-[tris(3-methylphenyl)phenylamino] triphenylamine (m-MTDATA), 4,4',4"-tris(N,N-diphenylamino)triphenylamine (TDATA), 4,4',4"-tris{N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(1-naphthalene-1-yl)-N,N'-diphenyl-benzidine (NPB), triphenylamine-containing polyetherketone (TPAPEK), 4-isopropyl-4'-methyldiphenyliodonium [tetrakis(pentafluorophenyl)borate], and/or dipyrazino[2,3-f:2',3'-h]quinoxaline-2,3,6,7,10,11-hexacarbonitrile (HAT-CN).

The hole transport layer HTL may include, for example, carbazole derivatives (such as N-phenyl carbazole and/or polyvinyl carbazole), fluorene-based derivatives, N,N'-bis(3-methylphenyl)-N,N'-diphenyl-[1,1-biphenyl]-4,4'-diamine (TPD), triphenylamine-based derivatives (such as 4,4',4"-tris(N-carbazolyl)triphenylamine (TCTA)), N,N'-di(1-naphthalene-1-yl)-N,N'-diphenyl-benzidine (NPB), 4,4'-cyclohexylidene bis[N,N-bis(4-methylphenyl)benzeneamine] (TAPC), 4,4'-bis[N,N'-(3-tolyl)amino]-3,3'-dimethylbiphenyl (HMTPD), 1,3-bis(N-carbazolyl)benzene (mCP), etc.

The thickness of the hole transport region HTR may be from about 50 Å to about 10,000 Å, for example, from about 100 Å to about 5,000 Å. The thickness of the hole injection layer HIL may be, for example, from about 30 Å to about 1,000 Å, and the thickness of the hole transport layer HTL may be from about 30 Å to about 1,000 Å. For example, the thickness of the electron blocking layer EBL may be from about 10 Å to about 1,000 Å. When the thicknesses of the hole transport region HTR, the hole injection layer HIL, the hole transport layer HTL and the electron blocking layer EBL each independently satisfy any of the above-described ranges, satisfactory (or suitable) hole transport properties may be achieved without substantial increase of a driving voltage.

The hole transport region HTR may further include a charge generating material, in addition to the above-described materials, to increase conductivity. The charge generating material may be dispersed uniformly or non-uniformly in the hole transport region HTR. The charge generating material may be, for example, a p-dopant. The p-dopant may be one of quinone derivatives, metal oxides, or cyano group-containing compounds, without limitation. Non-limiting examples of the p-dopant may include quinone derivatives (such as tetracyanoquinodimethane (TCNQ) and/or 2,3,5,6-tetrafluoro-7,7',8,8'-tetracyanoquinodimethane (F4-TCNQ)), metal oxides (such as tungsten oxide and/or molybdenum oxide), and inorganic metal compounds (such as CuI and/or RbI), without limitation.

As described above, the hole transport region HTR may further include at least one of a hole buffer layer or an electron blocking layer EBL, in addition to the hole injection layer HIL and the hole transport layer HTL. The hole buffer layer may compensate an optical resonance distance according to the wavelength of light emitted from an emission layer EML and may increase light emission efficiency. Any of the materials which may be included in a hole transport region HTR may be used as materials included in a hole buffer layer. The electron blocking layer EBL is a layer playing the role of preventing (or reducing) the electron injection from the electron transport region ETR to the hole transport region HTR.

The emission layer EML may be provided on the hole transport region HTR. The emission layer EML may have a thickness of, for example, about 100 Å to about 1,000 Å, or from about 100 Å to about 400 Å. The emission layer EML may have a single layer formed using a single material, a single layer formed using a plurality of different materials, or a multilayer structure having a plurality of layers formed using a plurality of different materials.

In the organic electroluminescence device 10 of an embodiment, the emission layer EML may include the compound of an embodiment.

Meanwhile, in the description, the term "substituted or unsubstituted" corresponds to a group that is unsubstituted or that is substituted with at least one substituent selected from the group consisting of a deuterium atom, a halogen atom, a cyano group, a nitro group, an amino group, a silyl group, an oxy group, a thio group, a sulfinyl group, a sulfonyl group, a carbonyl group, a boron group, a phosphine oxide group, a phosphine sulfide group, an alkyl group, an alkenyl group, an alkoxy group, a hydrocarbon ring group, an aryl group, and a heterocyclic group. In addition, each of the exemplified substituents may itself be substituted or unsubstituted. For example, a biphenyl group may be interpreted as an aryl group or a phenyl group substituted with a phenyl group.

In the description, the term "forming a ring via the combination with an adjacent group" may refer to forming a substituted or unsubstituted hydrocarbon ring, or a substituted or unsubstituted heterocycle via the combination with an adjacent group. The hydrocarbon ring includes an aliphatic hydrocarbon ring and an aromatic hydrocarbon ring. The heterocycle includes an aliphatic heterocycle and an aromatic heterocycle. The ring formed by the combination with an adjacent group may be a monocyclic ring or a polycyclic ring. In some embodiments, the ring formed via the combination with an adjacent group may be combined with another ring to form a spiro structure.

In the description, the term "adjacent group" may refer to a pair of substituent groups where the first substituent is connected to an atom which is directly connected to another atom substituted with the second substituent; a pair of substituent groups connected to the same atom; or a pair of substituent groups where the first substituent is sterically positioned at the nearest position to the second substituent. For example, in 1,2-dimethylbenzene, two methyl groups may be interpreted as "adjacent groups" to each other, and in 1,1-diethylcyclopentane, two ethyl groups may be interpreted as "adjacent groups" to each other.

In the description, examples of the halogen atom include a fluorine atom, a chlorine atom, a bromine atom, and an iodine atom.

In the description, the alkyl may be a linear, branched, or cyclic alkyl group. The carbon number of the alkyl may be 1 to 50, 1 to 30, 1 to 20, 1 to 10, or 1 to 6. Examples of the alkyl may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the description, the hydrocarbon ring may be an aliphatic hydrocarbon ring or an aromatic hydrocarbon ring of 5 to 60, 5 to 30, or 5 to 20 carbon atoms for forming a ring. The hydrocarbon ring group may be a functional group or substituent derived from an aliphatic hydrocarbon ring, or a functional group or substituent derived from an aromatic hydrocarbon ring. The carbon number of atoms for forming a ring of the hydrocarbon ring may be 5 to 60, 5 to 30, or 5 to 20.

In the description, the aryl group may refer to a functional group or substituent derived from an aromatic hydrocarbon ring. The aryl group may be a monocyclic aryl group or a polycyclic aryl group. The carbon number for forming a ring of the aryl group may be 6 to 30, 6 to 20, or 6 to 15. Examples of the aryl group may include phenyl, naphthyl, fluorenyl, anthracenyl, phenanthryl, biphenyl, terphenyl, quaterphenyl, quinquephenyl, sexaphenyl, triphenylenyl, pyrenyl, benzofluoranthenyl, chrysenyl, etc., without limitation.

In the description, the heterocyclic group may refer to a functional group or substituent derived from a ring including one or more heteroatoms selected from among B, O, N, P, Si and S. The heterocyclic group includes an aliphatic heterocyclic group and an aromatic heterocyclic group. The aromatic heterocyclic group may be a heteroaryl group. The aliphatic heterocycle (e.g., aliphatic heterocyclic group) and the aromatic heterocycle (e.g., aromatic heterocyclic group) may each independently be a monocycle or polycycle.

In the description, the heterocycle (e.g., heterocyclic group) may include one or more selected from among B, O, N, P, Si and S as heteroatoms. If the heterocycle includes two or more heteroatoms, the two or more heteroatoms may be the same or different. The heterocycle may be a monocyclic heterocycle or a polycyclic heterocycle and may include a heteroaryl group. The carbon number for forming a ring of the heterocycle may be 2 to 30, 2 to 20, or 2 to 10.

In the description, the aliphatic heterocyclic group may include one or more selected from among B, O, N, P, Si and S as heteroatoms. The carbon number for forming a ring of the aliphatic heterocyclic group may be 2 to 30, 2 to 20, or 2 to 10.

Examples of the aliphatic heterocyclic group include an oxirane group, a thiirane group, a pyrrolidine group, a piperidine group, a tetrahydrofuran group, a tetrahydrothiophene group, a thiane group, a tetrahydropyran group, a 1,4-dioxane group, etc., without limitation.

In the description, the heteroaryl group may include one or more selected from among B, O, N, P, Si and S as heteroatoms. If the heteroaryl group includes two or more heteroatoms, two or more heteroatoms may be the same or different. The heteroaryl group may be a monocyclic heteroaryl group or a polycyclic heteroaryl group. The carbon number for forming a ring of the heteroaryl group may be 2 to 30, 2 to 20, or 2 to 10. Examples of the heteroaryl group may include thiophene, furan, pyrrole, imidazole, triazole, pyridine, bipyridine, pyrimidine, triazine, acridine, pyridazine, pyrazine, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofuran, phenanthroline, thiazole, isooxazole, oxazole, oxadiazole, thiadiazole, phenothiazine, dibenzosilole, dibenzofuran, etc., without limitation.

In the description, the carbon number of the amine group is not specifically limited, but may be 1 to 30. The amine group may include an alkyl amine group, and an aryl amine group. Examples of the amine group include a methylamine group, a dimethylamine group, a phenylamine group, a diphenylamine group, a naphthylamine group, a 9-methylanthracenylamine group, a triphenylamine group, etc., without limitation. For example, the alkyl group in the alkyl amine group may be the same as the above-described alkyl group, and the aryl group in the aryl amine group may be the same as the above-described aryl group.

In the description, the direct linkage may refer to a single bond.

Meanwhile, in the description, "-*" may refer to a connected position (e.g., a binding site to a neighboring atom).

In the description, "atoms for forming a ring" may refer to ring-forming atoms.

An organic electroluminescence device 10 of an embodiment may include a compound of an embodiment, represented by the following Formula 1:

Formula 1

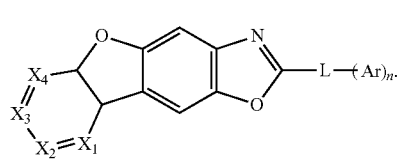

In Formula 1, $X_1$ to $X_4$ may each independently be $CR_a$.

That is, the compound of an embodiment, represented by Formula 1 may include a condensed ring structure of benzofuran and benzoxazole.

If $X_1$ to $X_4$ are $CR_a$, a plurality of $CR_a$ may each independently include a hydrogen atom, a deuterium atom, a halogen atom, a cyano group, a substituted or unsubstituted silyl group, a substituted or unsubstituted amine group, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, and/or combined with an adjacent group to form a ring. For example, $R_a$ in $CR_a$ may be a hydrogen atom, a substituted or unsubstituted aryl group of 6 to 20 carbon atoms for forming a ring, or a substituted or unsubstituted heteroaryl group of 2 to 20 carbon atoms for forming a ring, but an embodiment of the present disclosure is not limited thereto.

For example, if a plurality selected from $X_1$ to $X_4$ is represented by $CR_a$, a plurality of $R_a$ may be the same, or at least one thereof may be different. Meanwhile, neighboring $R_a$ groups among the plurality of $R_a$ may be combined with each other to form a hydrocarbon ring or a heterocycle.

In Formula 1, L may be a substituted or unsubstituted arylene group of 6 to 30 carbon atoms for forming a ring, or a substituted or unsubstituted heteroarylene group of 2 to 30 carbon atoms for forming a ring.

L may be a substituted or unsubstituted phenylene group, or a substituted or unsubstituted pyridylene group. For example, in Formula 1, L may be represented by L-1 or L-2:

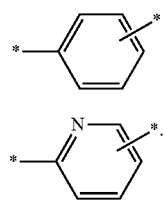

L-1

L-2

In the compound of an embodiment represented by Formula 1, Ar may be a substituted or unsubstituted hydrocarbon ring group of 6 to 30 carbon atoms for forming a ring, or a substituted or unsubstituted heterocyclic group of 2 to 30 carbon atoms for forming a ring. For example, Ar may be a substituted or unsubstituted aryl group of 6 to 20 carbon atoms for forming a ring, or a substituted or unsubstituted heteroaryl group of 2 to 20 carbon atoms for forming a ring. Ar may be an unsubstituted aryl group of 6 to 20 carbon atoms for forming a ring, or a substituted or unsubstituted heteroaryl group of 2 to 20 carbon atoms for forming a ring, which includes at least one selected from among N, O and B as a ring-forming atom.

In Formula 1, "n" may be 1 or 2. For example, in the compound of an embodiment, represented by Formula 1, Ar bonded to a linker L may be one or two (e.g., one or two Ar(s) may be bonded to L). Meanwhile, if "n" is 2, two Ar groups bonded to the linker may be the same or different.

The compound according to an embodiment may have a connected structure of a condensed ring of benzofuran and benzoxazole with a substituent hydrocarbon ring or heterocycle represented by "Ar" connected via a linker "L".

The condensed part of the present compound, obtained by condensing benzofuran and benzoxazole, may be an electron acceptor. In an embodiment, the compound may have a D (electron donor)-A (electron acceptor) structure. In this case, in the compound represented by Formula 1, the "Ar" group may be an electron donor. In some embodiments, in the compound represented by Formula 1, if "n" is 2, the compound according to an embodiment may include one electron acceptor and two electron donors.

For example, if Ar is a substituted or unsubstituted aryl group, Ar may be a substituted or unsubstituted phenyl group, a substituted or unsubstituted naphthyl group, a substituted or unsubstituted biphenyl group, or a substituted or unsubstituted triphenylene group. However, an embodiment of the present disclosure is not limited thereto.

In some embodiments, if Ar is a substituted or unsubstituted heteroaryl group, Ar may be a substituted or unsubstituted carbazolyl group, or a substituted or unsubstituted dibenzofuranyl group. However, an embodiment of the present disclosure is not limited thereto.

For example, Ar may be represented by the following Formula 2:

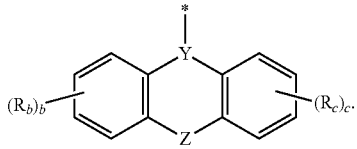

Formula 2

In Formula 2, Y may be N or B, and Z may be a direct linkage, O, S, $NR_d$, or $CR_eR_f$. In Formula 2, "b" and "c" may be each independently an integer of 0 to 4.

In Formula 2, $R_b$ to $R_f$ may be each independently a hydrogen atom, a deuterium atom, a halogen atom, a cyano group, a substituted or unsubstituted silyl group, a substituted or unsubstituted amine group, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, and/or combined with an adjacent group to form a ring.

If "b" is an integer of 2 or more, a plurality of $R_b$ may be the same, or at least one thereof may be different. If "c" is an integer of 2 or more, a plurality of $R_c$ may be the same, or at least one thereof may be different.

Meanwhile, if $R_b$ to $R_f$ are combined with an adjacent group to form a ring, adjacent substituents selected from among $R_b$ to $R_f$ may be combined with each other to form a hydrocarbon ring or a heterocycle. The ring formed by combining adjacent substituents may be condensed with the hydrocarbon ring or heterocycle core of Ar.

Ar represented by Formula 2 may be represented by the following Formula 2-1 or Formula 2-2:

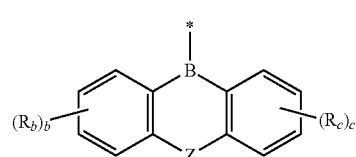

Formula 2-1

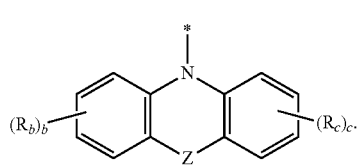

Formula 2-2

In Formula 2-1 and Formula 2-2, the same explanation for Z, $R_b$, $R_c$, "b", and "c" as provided in connection with Formula 2 may be applied.

Meanwhile, Formula 2-2 may be represented by any one among the following Formula 2-2A to Formula 2-2E:

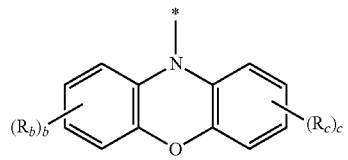

Formula 2-2A

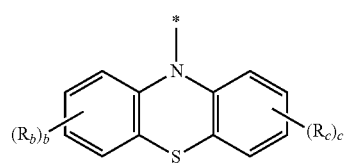

Formula 2-2B

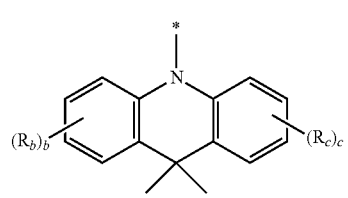

Formula 2-2C

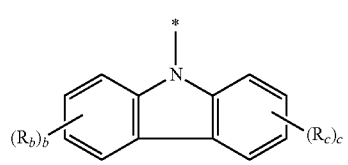

Formula 2-2D

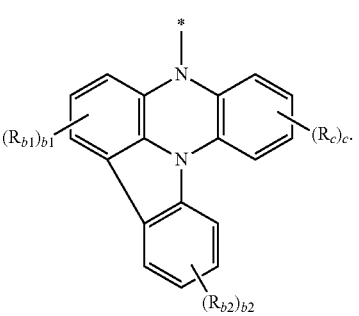

Formula 2-2E

In Formula 2-2E, "b1" may be an integer of 0 to 3, and "b2" may be an integer of 0 to 4. In addition, $R_{b1}$ and $R_{b2}$ may be each independently a hydrogen atom, a deuterium atom, a halogen atom, a cyano group, a substituted or unsubstituted silyl group, a substituted or unsubstituted amine group, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, and/or combined with an adjacent group to form a ring.

In Formula 2-2A to Formula 2-2E, the same explanation for $R_b$, $R_c$, "b", and "c" as provided in connection with Formula 2 may be applied.

In some embodiments, Formula 1 may be represented by the following Formula 1-1:

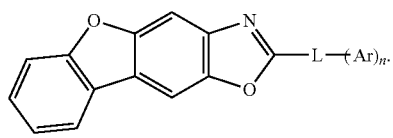

Formula 1-1

In Formula 1-1, the same explanation for L, "n" and Ar as provided in connection with Formula 1 may be applied.

In the compound of an embodiment represented by Formula 1, for example, if "Ar" is represented by Formula 2-2, the compound of an embodiment may be a material emitting delayed fluorescence of a D-A type (or kind). The compound according to an embodiment may be a material emitting thermally activated delayed fluorescence (TADF) of a D-A type (or kind) including a condensed part (e.g., condensed portion), in which benzofuran and benzoxazole are condensed, as an electron acceptor, and a part (e.g., portion) represented by Formula 2-2 as an electron donor.

The compound of an embodiment may be any one among the compounds represented in Compound Group 1 below. The organic electroluminescence device 10 of an embodiment may include at least one compound among the compounds represented in Compound Group 1 in an emission layer EML.

Compound Group 1

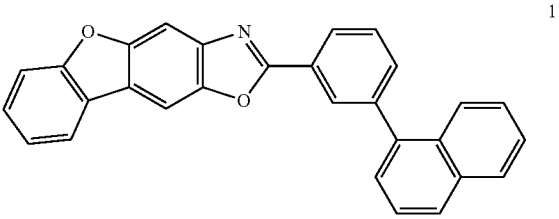

1

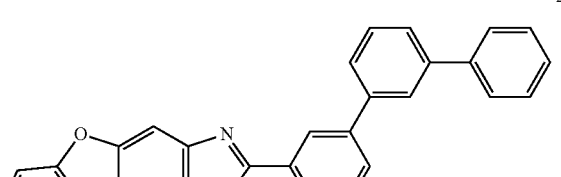

2

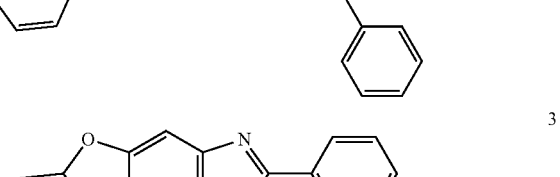

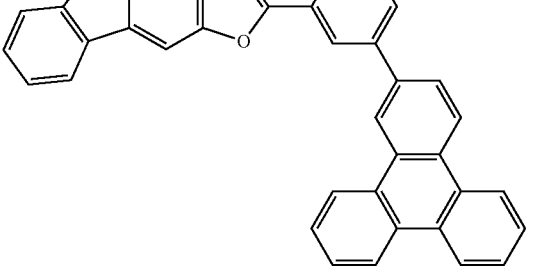

3

4
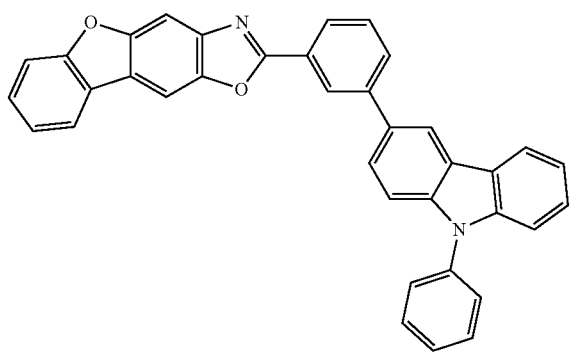
5
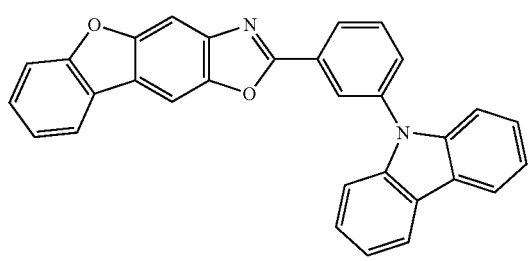
6
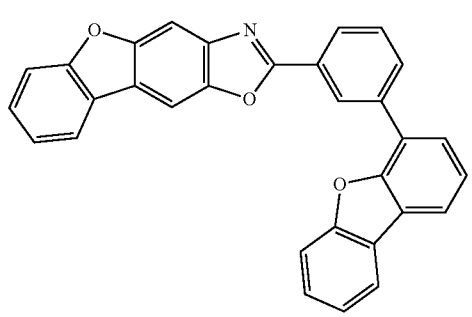
7
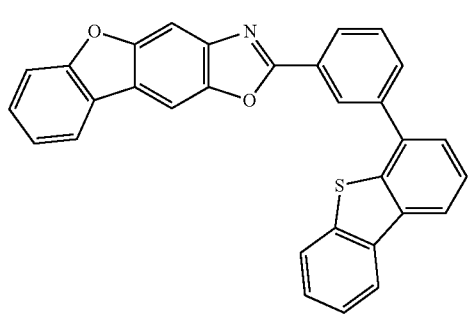
8
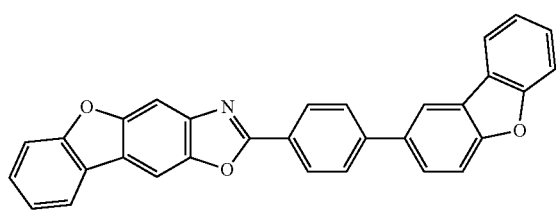
9
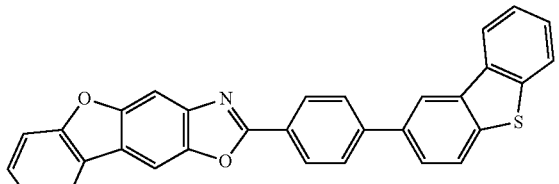
10
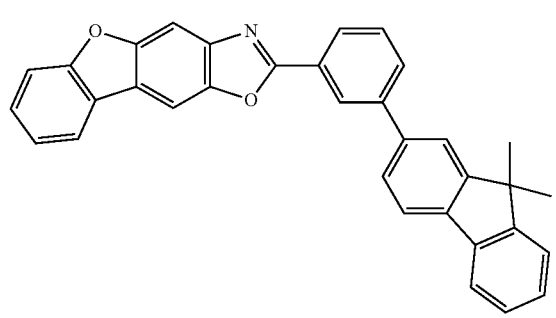
11
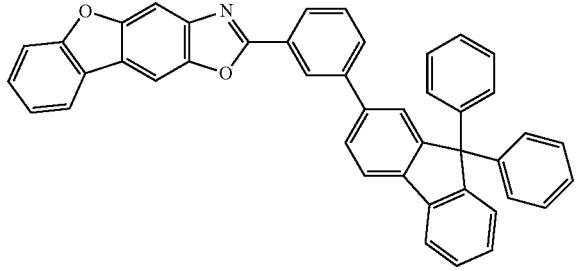
12
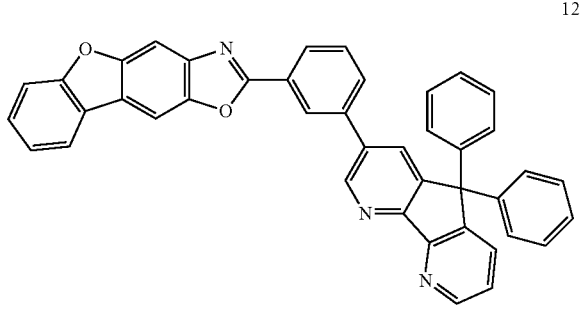
13
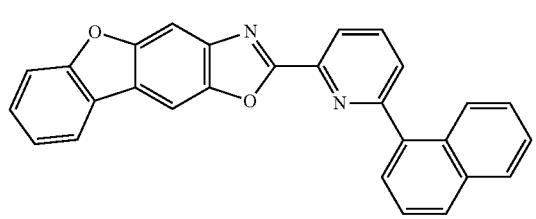

14
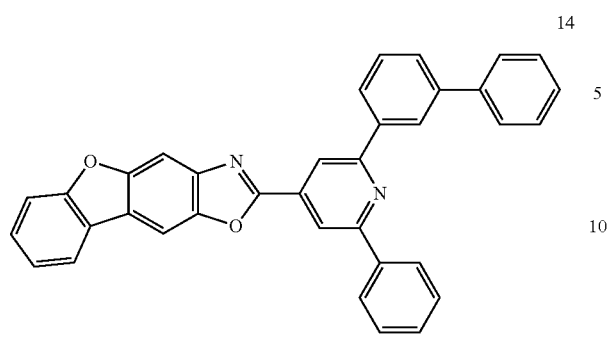
15
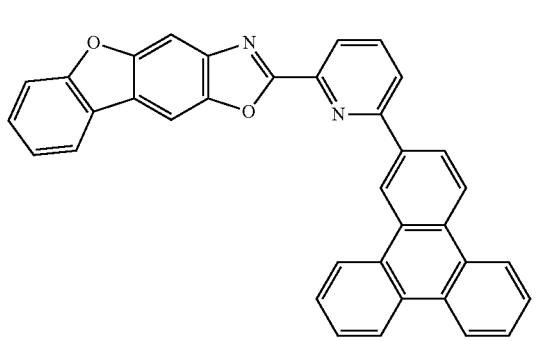
16
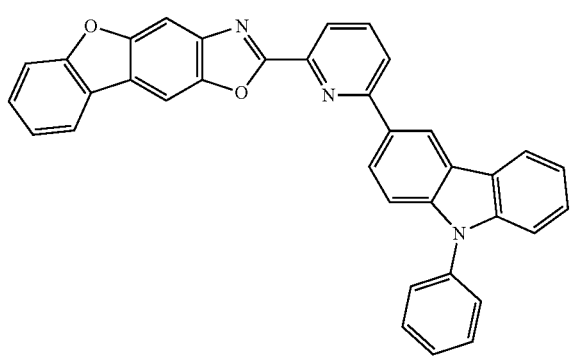
17
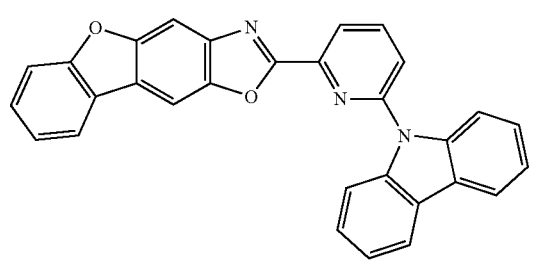
18
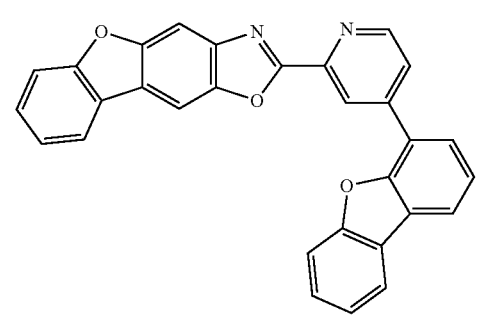
25
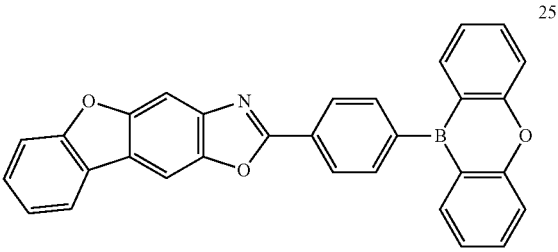
26
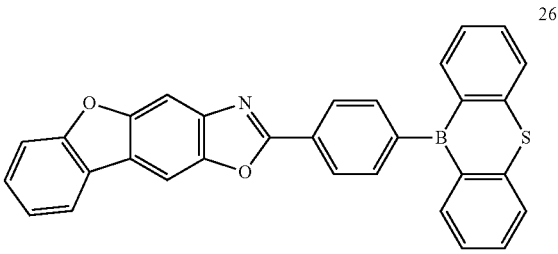
27
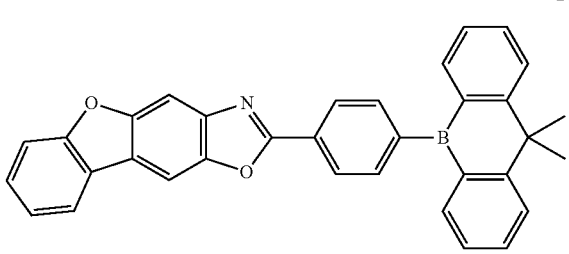
28
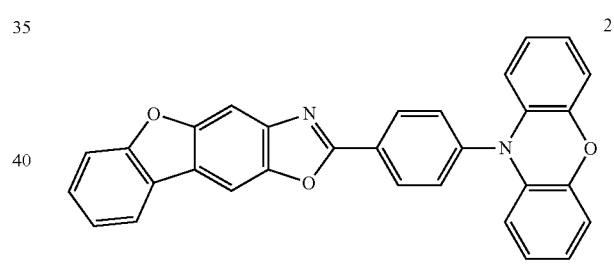
29
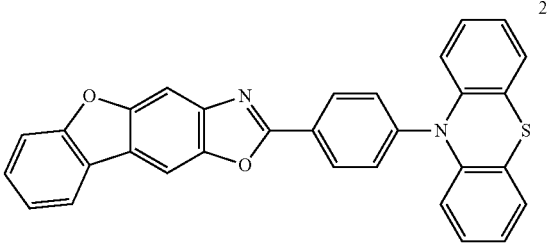
30
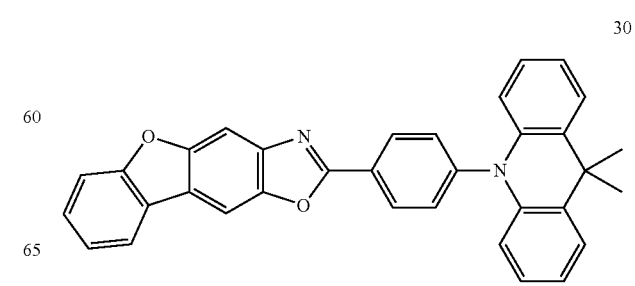

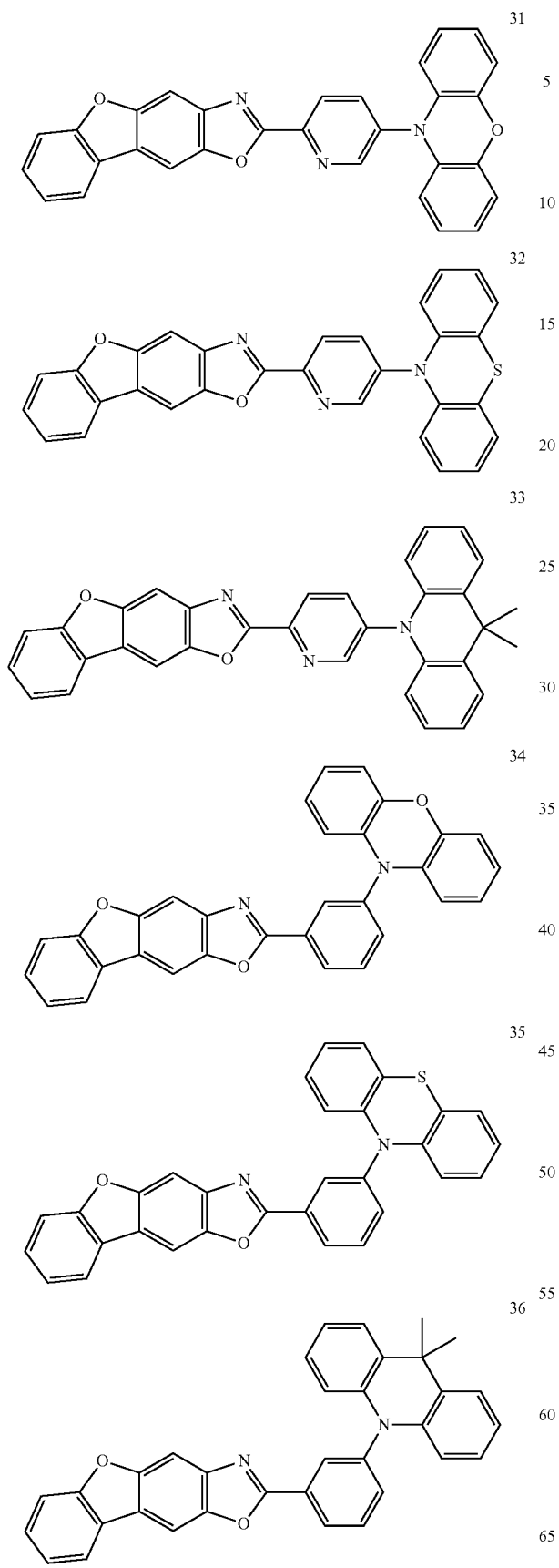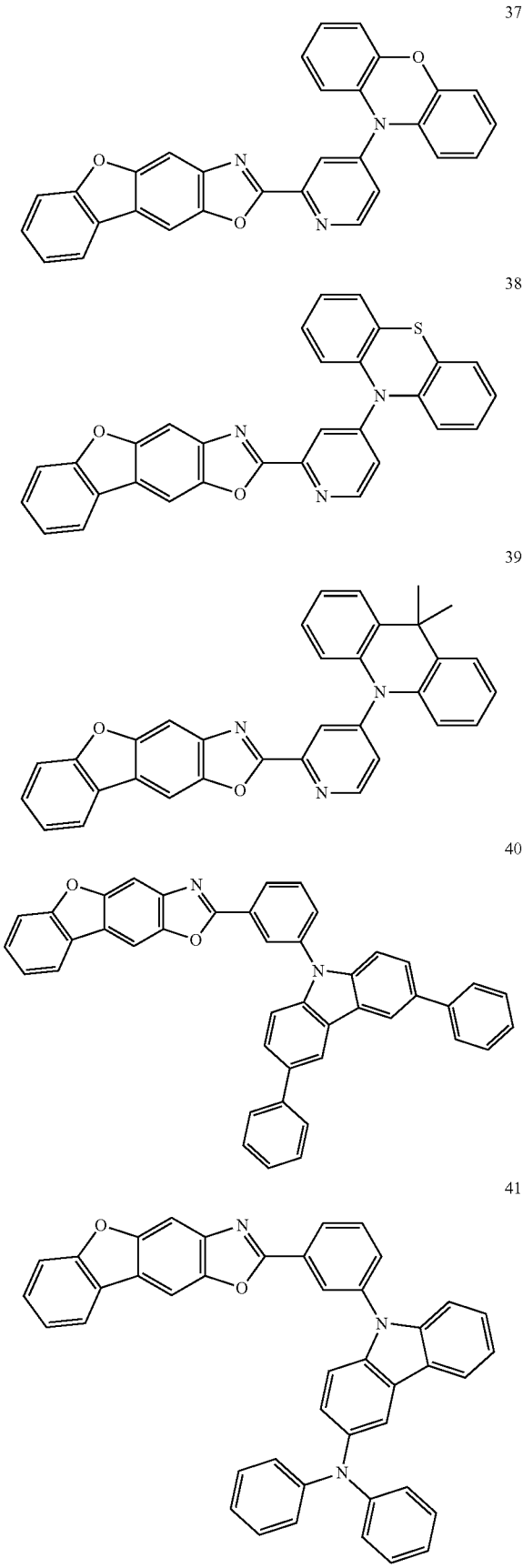

42
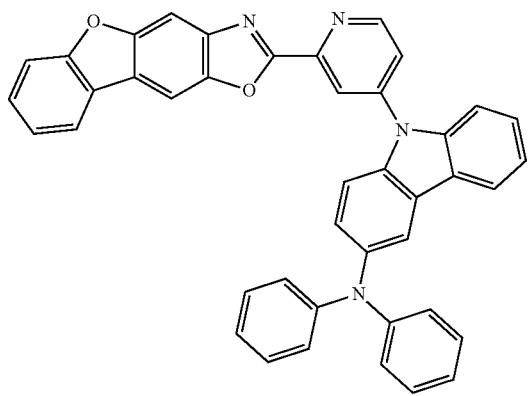
43
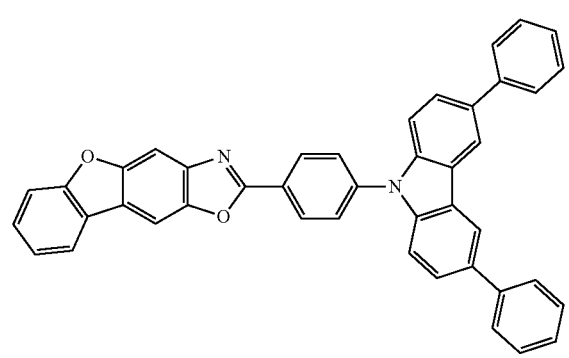
44
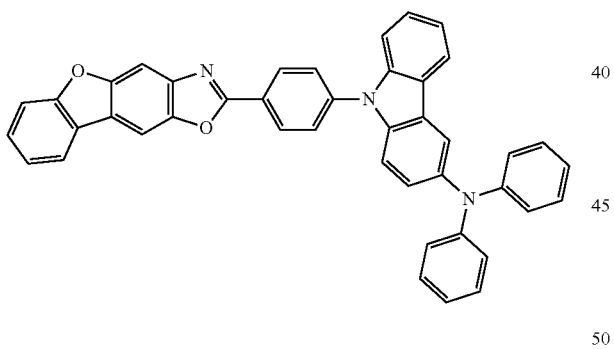
45
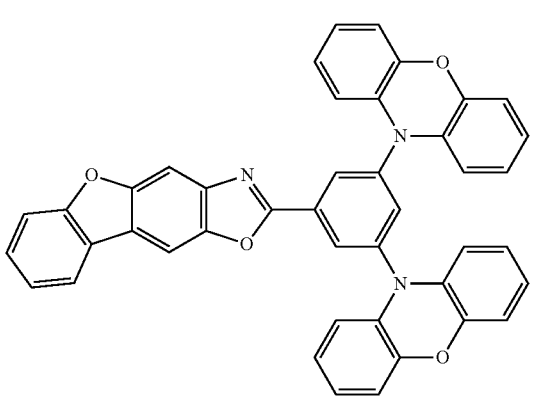
46
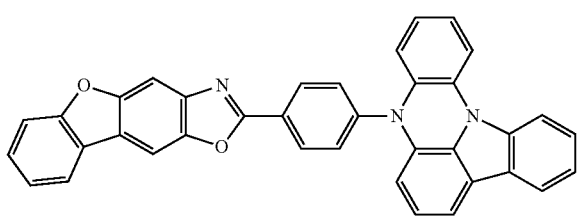
47
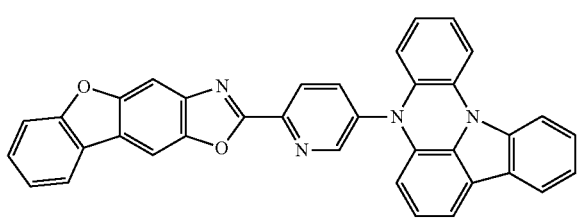
48
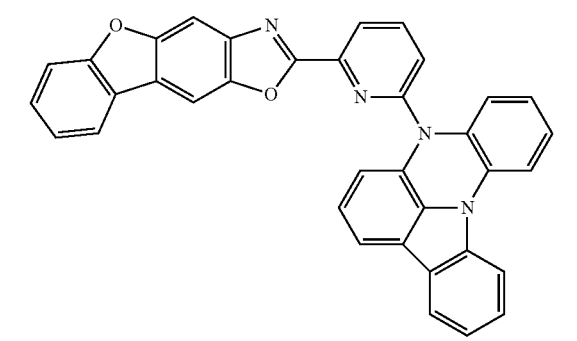
52
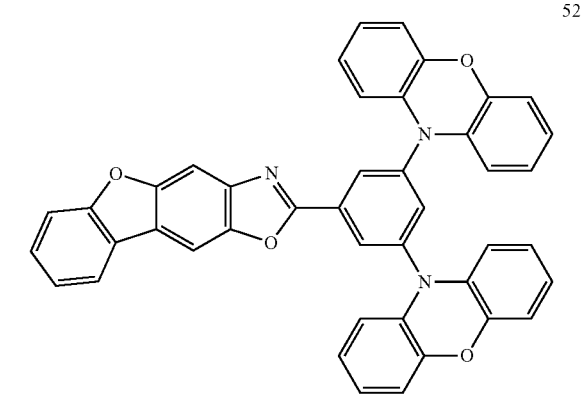
53
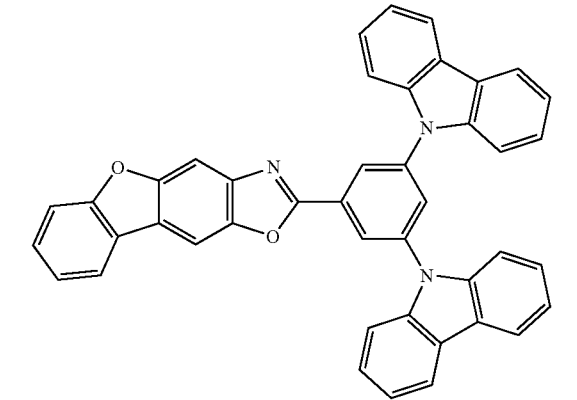

54

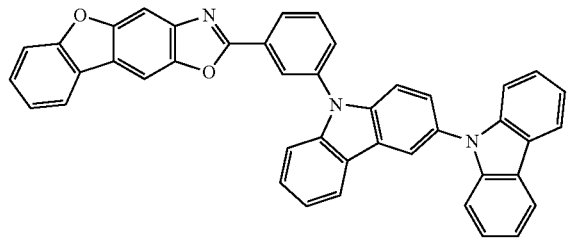

55

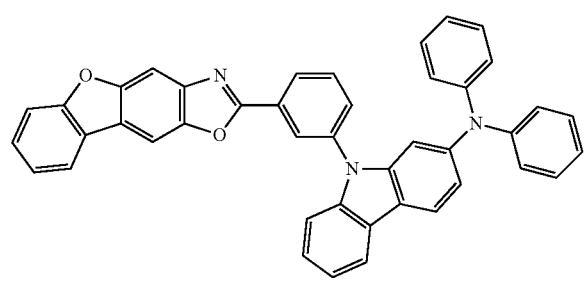

56

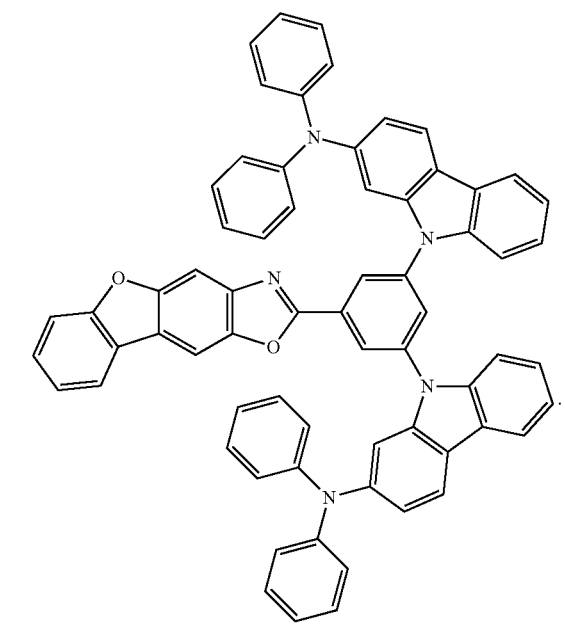

The compound according to an embodiment may be a light-emitting material having a light-emitting central wavelength ($\lambda_{max}$) of about 420 nm or more. For example, the compound of an embodiment represented by Formula 1 may be a light emitting material having a light-emitting central wavelength of about 420 nm to about 470 nm, or a light emitting material having a light-emitting central wavelength of about 500 nm to about 550 nm. The compound of an embodiment represented by Formula 1 may be a blue color dopant or a green color dopant.

In the organic electroluminescence device 10 of an embodiment, the emission layer EML includes a host and a dopant and may include the aforementioned compound of an embodiment as the dopant. For example, in the organic electroluminescence device 10 of an embodiment, the emission layer EML may include the aforementioned compound of an embodiment as a dopant for emitting delayed fluorescence.

The compound represented by Formula 1 has an absolute value ($\Delta E_{ST}$) of a difference between the lowest excitation singlet energy level (S1) and the lowest excitation triplet energy level (T1) of about 0.2 eV or less, and may be used as a thermally activated delayed fluorescence dopant. Accordingly, the organic electroluminescence device 10 of an embodiment may include at least one selected from among the aforementioned compounds of the present embodiments in an emission layer EML as a thermally activated delayed fluorescence (TADF) dopant, and the emission layer EML may emit delayed fluorescence. For example, the emission layer EML may emit thermally activated delayed fluorescence.

The compound of an embodiment has a novel (e.g., improved) compound structure including a condensed ring of benzoxazole and benzofuran as an electron acceptor, and may be used as a material emitting thermally activated delayed fluorescence. The compound of an embodiment may be used as a material for the emission layer of an organic electroluminescence device and may improve the emission efficiency and increase the life of the organic electroluminescence device. Particularly, the compound according to an embodiment may be used as a light-emitting material emitting light in blue or green wavelength region and may show excellent emission efficiency.

In an embodiment, the emission layer EML may be a delayed fluorescence emission layer, and the emission layer EML may include any suitable host material and the aforementioned compound of an embodiment. For example, in an embodiment, the emission layer EML may include the compound of an embodiment as a dopant material and may include, as a host material, tris(8-hydroxyquinolino)aluminum ($Alq_3$), 4,4'-bis(N-carbazolyl)-1,1'-biphenyl (CBP), poly(N-vinylcarbazole) (PVK), 9,10-di(naphthalene-2-yl)anthracene (ADN), 4,4',4"-tris(carbazol-9-yl)-triphenylamine (TCTA), 1,3,5-tris(1-phenyl-1H-benzo[d]imidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl]ether oxide (DPEPO), hexaphenyl cyclotriphosphazene (CP1), 1,4-bis(triphenylsilyl)benzene (UGH2), hexaphenylcyclotrisiloxane ($DPSiO_3$), octaphenylcyclotetrasiloxane ($DPSiO_4$), 2,8-bis(diphenylphosphoryl)dibenzo[b,d]furan (PPF), 3,3'-bis(N-carbazolyl)-1,1'-biphenyl (mCBP), 1,3-bis(N-carbazolyl)benzene (mCP), etc. However, an embodiment of the present disclosure is not limited thereto, and any suitable host materials for emitting delayed fluorescence may be included, for example, in addition to the above-described host materials.

However, an embodiment of the present disclosure is not limited thereto, and the compound of an embodiment may be used as the host material of the emission layer EML. If the compound of an embodiment is used as the host material, any suitable dopant material may be used in addition to the compound of an embodiment in the emission layer EML.

In the organic electroluminescence device 10 of an embodiment, the emission layer EML may include as the dopant material, styryl derivatives (for example, 1,4-bis[2-(3-N-ethylcarbazolyl)vinyl]benzene (BCzVB), 4-(di-p-tolylamino)-4'-[(di-p-tolylamino)styryl]stilbene (DPAVB), and/or N-(4-((E)-2-(6-((E)-4-(diphenylamino)styryl)naphthalen-2-yl)vinyl)phenyl)-N-phenylbenzenamine (N-BDAVBi)), perylene and/or the derivatives thereof (for example, 2,5,8, 11-tetra-t-butylperylene (TBP)), pyrene and/or the derivatives thereof (for example, 1,1-dipyrene, 1,4-dipyrenylbenzene, 1,4-bis(N,N-diphenylamino)pyrene), 1,2,3,5-tetrakis (carbazol-9-yl)-4,6-dicyanobenzene (4-CzIPN), etc.

If the emission layer EML emits blue light, the emission layer EML may further include a fluorescence material including any one selected from the group consisting of spiro-DPVBi, spiro-6P, distyryl-benzene (DSB), distyryl-arylene (DSA), a polyfluorene (PFO)-based polymer and a poly(p-phenylene vinylene)-based polymer. If the emission layer EML emits blue light, the emission layer EML may include, for example, the compound of an embodiment as a host material and a metal complex, an organometallic complex (such as (4,6-F2ppy)2Irpic), perylene and/or the derivatives thereof, etc. as the dopant material.

If the emission layer EML emits green light, the emission layer EML may further include a fluorescence material including tris(8-hydroxyquinolinato)aluminum ($Alq_3$). If the emission layer EML emits green color, the emission layer EML may include, for example, the compound of an embodiment as a host material, and a metal complex, an organometallic complex (such as fac-tris(2-phenylpyridine) iridium ($Ir(ppy)_3$)), coumarin and/or the derivatives thereof, etc. as the dopant material.

In some embodiments, the organic electroluminescence device 10 of an embodiment may include a plurality of emission layers. The plurality of emission layers may be provided by stacking in order. For example, an organic electroluminescence device 10 including a plurality of emission layers may emit white light. The organic electroluminescence device including a plurality of emission layers may be an organic electroluminescence device of a tandem structure. In case where an organic electroluminescence device 10 includes a plurality of emission layers, at least one emission layer EML may include the above-described compound of an embodiment.

In the organic electroluminescence devices 10 of an embodiment, shown in FIG. 1 to FIG. 4, an electron transport region ETR is provided on an emission layer EML. The electron transport region ETR may include at least one of a hole blocking layer HBL, an electron transport layer ETL or an electron injection layer EIL. However, an embodiment of the present disclosure is not limited thereto.

The electron transport region ETR may have a single layer formed using a single material, a single layer formed using a plurality of different materials, or a multilayer structure having a plurality of layers formed using a plurality of different materials.

For example, the electron transport region ETR may have a single layer structure of an electron injection layer EIL or an electron transport layer ETL, or a single layer structure formed using an electron injection material and an electron transport material. In some embodiments, the electron transport region ETR may have a single layer structure having a plurality of different materials, or a structure stacked from the emission layer EML of electron transport layer ETL/ electron injection layer EIL, or hole blocking layer HBL/ electron transport layer ETL/electron injection layer EIL, without limitation. The thickness of the electron transport region ETR may be, for example, from about 300 Å to about 1,500 Å.

The electron transport region ETR may be formed using one or more suitable methods such as a vacuum deposition method, a spin coating method, a cast method, a Langmuir-Blodgett (LB) method, an inkjet printing method, a laser printing method, and/or a laser induced thermal imaging (LITI) method.

If the electron transport region ETR includes an electron transport layer ETL, the electron transport region ETR may include an anthracene-based compound. The electron transport region may include, for example, tris(8-hydroxyquinolinato)aluminum ($Alq_3$), 1,3,5-tri[(3-pyridyl)-phen-3-yl] benzene, 2,4,6-tris(3'-(pyridin-3-yl)biphenyl-3-yl)-1,3,5-triazine, 2-(4-(N-phenylbenzoimidazolyl-1-yl)phenyl)-9,10-dinaphthylanthracene, 1,3,5-tri(1-phenyl-1H-benzo[d] imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), berylliumbis(benzoquinolin-10-olate (Bebq$_2$), 9,10-di(naphthalene-2-yl)anthracene (ADN), 1,3-bis[3,5-di(pyridin-3-yl)phenyl]benzene (BmPyPhB), or a mixture thereof, without limitation. The thickness of the electron transport layer ETL may be from about 100 Å to about 1,000 Å and may be, for example, from about 150 Å to about 500 Å. When the thickness of the electron transport layer ETL satisfies any of the above-described ranges, satisfactory (or suitable) electron transport properties may be obtained without substantial increase of a driving voltage.

If the electron transport region ETR includes an electron injection layer EIL, the electron transport region ETR may include a metal halide (such as LiF, NaCl, CsF, RbCl, RbI, and/or CuI), a metal in lanthanoides (such as Yb), a metal oxide (such as $Li_2O$ and/or BaO), and/or 8-hydroxyquinolinato-lithium (Liq). However, an embodiment of the present disclosure is not limited thereto. The electron injection layer EIL may be formed using a mixture material of an electron transport material and an insulating organo metal salt. The insulating organo metal salt may be a material having an energy band gap of about 4 eV or more. The insulating organo metal salt may include, for example, metal acetate(s), metal benzoate(s), metal acetoacetate(s), metal acetylacetonate(s), and/or metal stearate(s). The thickness of the electron injection layer EIL may be from about 1 Å to about 100 Å, for example, from about 3 Å to about 90 Å. When the thickness of the electron injection layer EIL satisfies any of the above described ranges, satisfactory (or suitable) electron injection properties may be obtained without inducing substantial increase of a driving voltage.

The electron transport region ETR may include a hole blocking layer HBL as described above. The hole blocking layer HBL may include, for example, at least one of 2,9-dimethyl-4,7-diphenyl-1,10-phenanthroline (BCP), or 4,7-diphenyl-1,10-phenanthroline (Bphen). However, an embodiment of the present disclosure is not limited thereto.

The second electrode EL2 may be provided on the electron transport region ETR. The second electrode EL2 may be a common electrode and/or a cathode. The second electrode EL2 may be a transmissive electrode, a transflective electrode or a reflective electrode. If the second electrode EL2 is the transmissive electrode, the second electrode EL2 may include a transparent metal oxide, for example, ITO, IZO, ZnO, ITZO, etc.

If the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The second electrode EL2 may have a multilayer structure including a reflective layer or a transflective layer formed using any of the above-described materials and a transparent conductive layer formed using ITO, IZO, ZnO, ITZO, etc.

In some embodiments, the second electrode EL2 may be connected with an auxiliary electrode. When the second electrode EL2 is connected with the auxiliary electrode, the resistance of the second electrode EL2 may decrease.

Meanwhile, on the second electrode EL2 of the organic electroluminescence device 10 of an embodiment, a capping layer CPL may be further provided. The capping layer CPL may include, for example, α-NPD, NPB, TPD, m-MT-DATA, Alq$_3$, CuPc, N4,N4,N4',N4'-tetra(biphenyl-4-yl)biphenyl-4,4'-diamine (TPD15), 4,4',4''-tris(carbazol-9-yl)triphenylamine (TCTA), etc.

The organic electroluminescence device 10 according to an embodiment of the present disclosure may include the compound of an embodiment in the emission layer EML between the first electrode EU and the second electrode EL2 and may show improved emission efficiency. The compound according to an embodiment may be a thermally activated delayed fluorescence dopant, and the emission layer EML may include the compound of an embodiment and emit thermally delayed fluorescence, thereby showing excellent (or improved) emission efficiency properties. For example, the compound according to an embodiment may be used as the dopant material of the emission layer EML, and an organic electroluminescence device having excellent (or improved) emission efficiency and long-life characteristics in a green emission region or a blue emission region may be accomplished.

In some embodiments, the compound according to an embodiment may be included as the host material of the emission layer EML and may be used with a suitable fluorescence dopant material or a suitable phosphorescence dopant material, thereby improving the emission efficiency and life of the organic electroluminescence device.

Meanwhile, the aforementioned compound of an embodiment may be included in an organic layer other than the emission layer EML as a material for an organic electroluminescence device 10. For example, the organic electroluminescence device 10 according to an embodiment of the present disclosure may include the compound in at least one functional layer between the first electrode EL1 and the second electrode EL2, or a capping layer CPL positioned on the second electrode EL2.

The compound of an embodiment has a novel compound structure including a condensed ring of benzoxazole and benzofuran as an electron acceptor, and may be used as a material for an emission layer, thereby contributing to the increase of the efficiency properties of an organic electroluminescence device. In addition, the organic electroluminescence device of an embodiment, including the compound of an embodiment in an emission layer may show high efficiency properties in a green light-emitting wavelength region or a blue light-emitting wavelength region.

Hereinafter, the compound according to an embodiment of the present disclosure and the organic electroluminescence device of an embodiment will be particularly explained referring to embodiments and comparative embodiments. However, the following embodiments are only illustrations to assist the understanding of the present disclosure, and the scope of the present disclosure is not limited thereto.

EXAMPLES

1. Synthesis of Compounds of Embodiments

First, the synthetic methods of the compounds according to embodiments of the present disclosure will be explained in more detail by referring to the synthetic methods of Compounds 1, 3, 5, 30, 34, 52, 55 and 56. However, the synthetic methods of the compounds explained below are only example embodiments, and the synthetic method of the compound according to an embodiment of the present disclosure is not limited thereto.

(1) Synthesis of Compound 5

Compound 5 according to an embodiment may be synthesized, for example, by the steps (acts) of the following Reaction 1:

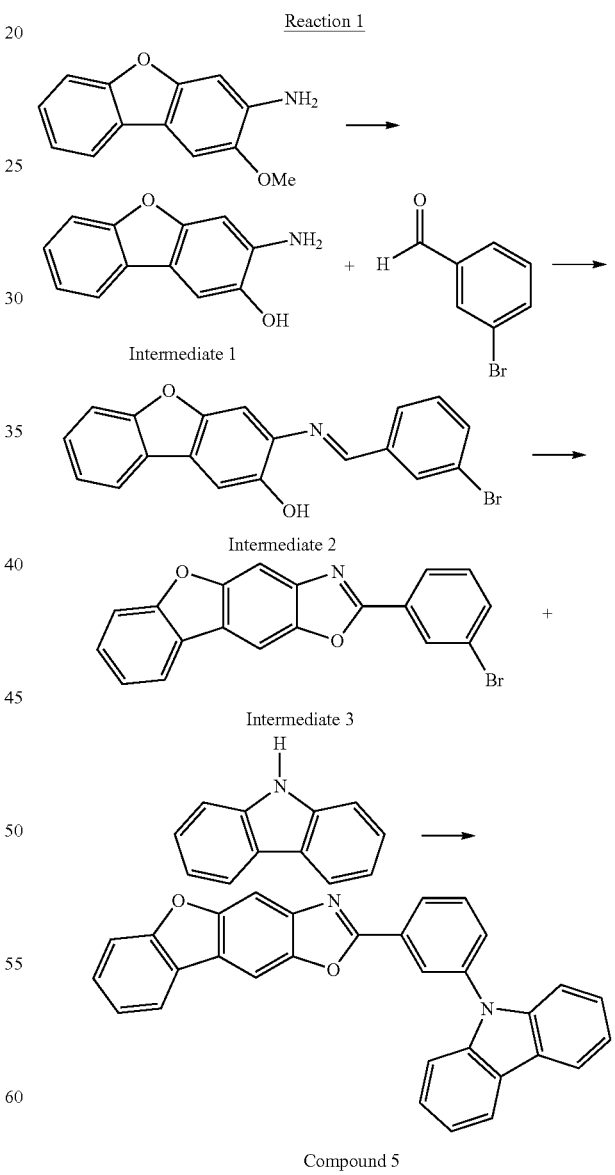

Reaction 1

Compound 5

Synthesis of Intermediate 1

To a one-neck 3,000 ml flask, 30.0 g (140.7 mmol) of 2-methoxydibenzo[b,d]furan-3-amine and 703 ml of dichloromethane(DCM) were added, and the resultant product was cooled to about 0° C. 105.7 g (422.08 mmol) of boron tribromide was diluted in 422 ml of dichloromethane, and the resulting boron tribromide solution (1.0 M DCM solution) was slowly added to the flask at about 0° C. Stirring was performed at about 0° C. for about 1 hour and then, at room temperature for about 4 hours. After finishing the reaction, the resultant product was cooled to about 0° C., and 300 ml of distilled water was slowly added thereto. 80.0 g (578.0 mmol) of K$_2$CO$_3$ was dissolved in 289 ml of distilled water and then slowly added thereto at about 0° C., and pH was adjusted to 7 to 8, followed by stirring at about 0° C. for one day. The solid thus precipitated was washed with distilled water, filtered, and dried in a vacuum oven for one day. 31.5 g (crude) of a gray solid compound (Intermediate 1) was obtained. Next reaction was performed without additional separation.

Synthesis of Intermediate 2

In a one-neck 1,000 ml flask, 12.8 g (64.3 mmol) of Intermediate 1, 14.3 g (77.1 mmol) of 3-bromobenzaldehyde and 321 ml of ethanol were mixed and stirred at room temperature for about 3 hours. After finishing the reaction, the solid thus precipitated was filtered while washing with ethanol. 19.0 g (yield: 80.7%) of a yellow solid compound (Intermediate 2) was obtained.

Synthesis of Intermediate 3

To a one-neck 1,000 ml flask, 19.0 g (51.8 mmol) of Intermediate 2 and 517 ml of dichloromethane were added and stirred at room temperature. 14.1 g (62.1 mmol) of 2,3-dichloro-5,6-dicyano-p-benzoquinone (DDQ) was slowly added thereto and stirred at room temperature for one day. After finishing the reaction, the reaction product was passed through a celite pad using hot chloroform, and solvents were removed using distillation under a reduced pressure. The compound thus obtained was made into a slurry using chloroform and methanol, and then, filtered using methanol. 17.6 g (yield: 93.36%) of a beige solid compound (Intermediate 3) was obtained.

Synthesis of Compound 5

In a one-neck 250 ml flask, 1.6 g (4.5 mmol) of Intermediate 3, 1.5 g (9.0 mmol) of 9H-carbazole, 0.3 g (0.5 mmol) of Pd(dba)$_2$, 0.26 g (0.5 mmol, 50 wt % toluene solution) of P(t-Bu)$_3$, 1.5 g (15.8 mmol) of NaOtBu and 45 ml of xylene were refluxed and stirred for one day. After cooling at room temperature, impurities were removed through celite filtering. After completely removing solvents, the crude product was separated by silica gel column chromatography (MC:Hex=1:8→1:1). The solid thus obtained was solidified (acetone:MeOH=2:1) and filtered to obtain 1.44 g (yield: 71%) of Compound 5 as a reddish brown solid. The measured value of the molecular weight of Compound 5 measured by Fast Atom Bombardment-Mass Spectrometry (FAB-MS) was MS[M+H]$^+$=451.

(2) Synthesis of Compound 30

Compound 30 according to an embodiment may be synthesized, for example, by the steps (acts) of the following Reaction 2:

Reaction 2

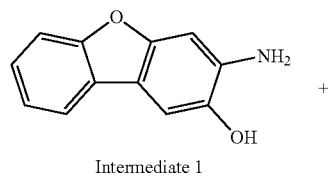

Intermediate 1

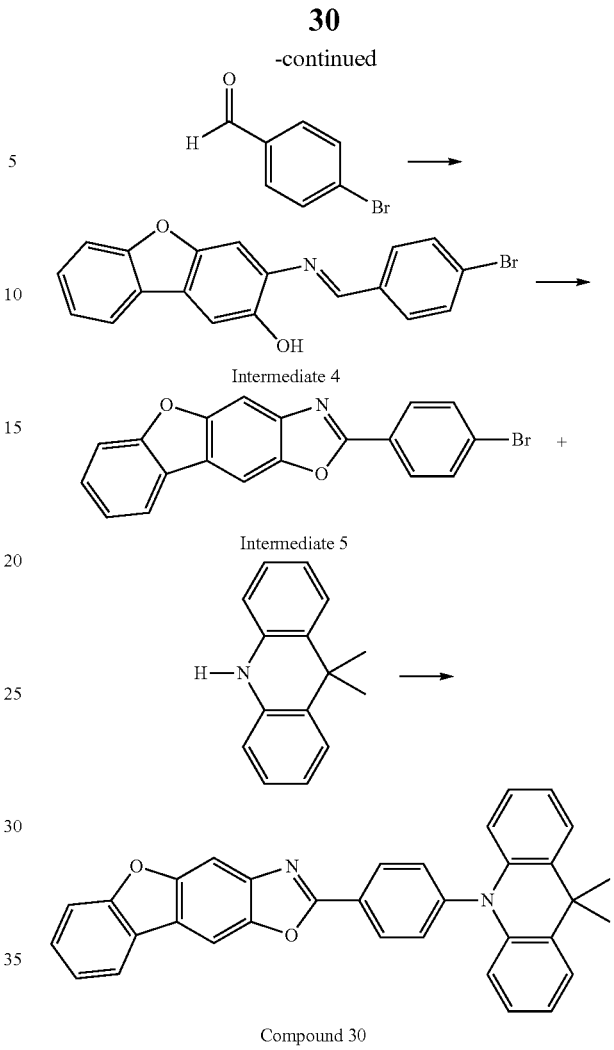

Compound 30

Synthesis of Intermediate 4

In a one-neck 1,000 ml flask, 12.8 g (64.3 mmol) of Intermediate 1, 14.3 g (77.1 mmol) of 4-bromobenzaldehyde and 321 ml of ethanol were mixed and stirred at room temperature for about 3 hours. After finishing the reaction, the solid thus precipitated was filtered while washing with ethanol. 18.5 g (yield: 79.1%) of a yellow solid compound (Intermediate 4) was obtained.

Synthesis of Intermediate 5

To a one-neck 1,000 ml flask, 18.5 g (50.8 mmol) of Intermediate 4 and 517 ml of dichloromethane were added and stirred at room temperature. 14.1 g (62.1 mmol) of 2,3-dichloro-5,6-dicyano-p-benzoquinone (DDQ) was slowly added thereto and stirred at room temperature for one day. After finishing the reaction, the reaction product was passed through a celite pad using hot chloroform, and solvents were removed using distillation under a reduced pressure. The compound thus obtained was made into a slurry using chloroform and methanol, and then, filtered using methanol. 16.8 g (yield: 91.1%) of a beige solid compound (Intermediate 5) was obtained.

Synthesis of Compound 30

In a one-neck 250 ml flask, 1.6 g (4.5 mmol) of Intermediate 5, 1.9 g (9.1 mmol) of 9,9-dimethyl-9,10-dihydroacridine, 0.3 g (0.5 mmol) of Pd(dba)$_2$, 0.26 g (0.5 mmol, 50 wt % toluene solution) of P(t-Bu)$_3$, 1.5 g (15.8 mmol) of NaOtBu and 45 ml of xylene were refluxed and stirred for one day. After cooling at room temperature, impurities were removed through celite filtering. After completely removing solvents, the crude product was separated by silica gel column chromatography (MC:Hex=1:8→1:1). The product thus obtained was solidified (acetone:MeOH=2:1) and filtered to obtain 1.66 g (yield: 75%) of Compound 30 as a reddish brown solid. The measured value of the molecular weight of Compound 30 measured by FAB-MS was MS[M+H]$^+$=493.

(3) Synthesis of Compound 34

Compound 34 according to an embodiment may be synthesized, for example, by the steps (acts) of the following Reaction 3:

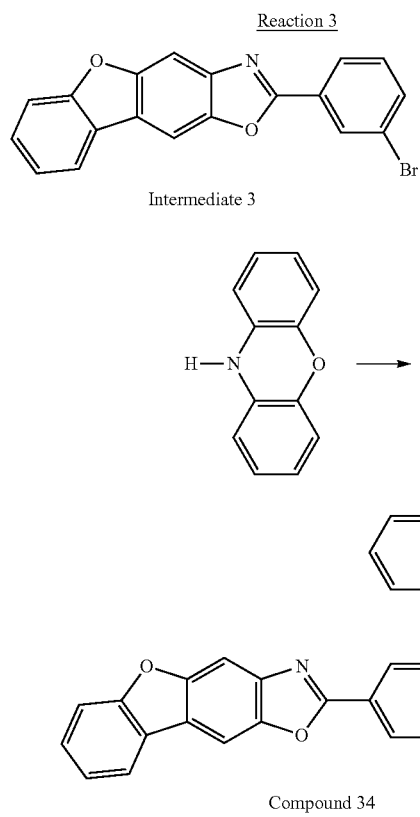

In a one-neck 250 ml flask, 1.6 g (4.5 mmol) of Intermediate 3, 1.65 g (9.0 mmol) of 10H-phenoxazine, 0.3 g (0.5 mmol) of Pd(dba)$_2$, 0.26 g (0.5 mmol, 50 wt % toluene solution) of P(t-Bu)$_3$, 1.5 g (15.8 mmol) of NaOtBu and 45 ml of xylene were refluxed and stirred for one day. After cooling at room temperature, impurities were removed through celite filtering. After completely removing solvents, the crude product was separated by silica gel column chromatography (MC:Hex=1:8→1:1). The product thus obtained was solidified (acetone:MeOH=2:1) and filtered to obtain 1.51 g (yield: 72%) of Compound 34 as a reddish brown solid. The measured value of the molecular weight of Compound 34 measured by FAB-MS was MS[M+H]$^+$=467.

(4) Synthesis of Compound 52

Compound 52 according to an embodiment may be synthesized, for example, by the steps (acts) of the following Reaction 4:

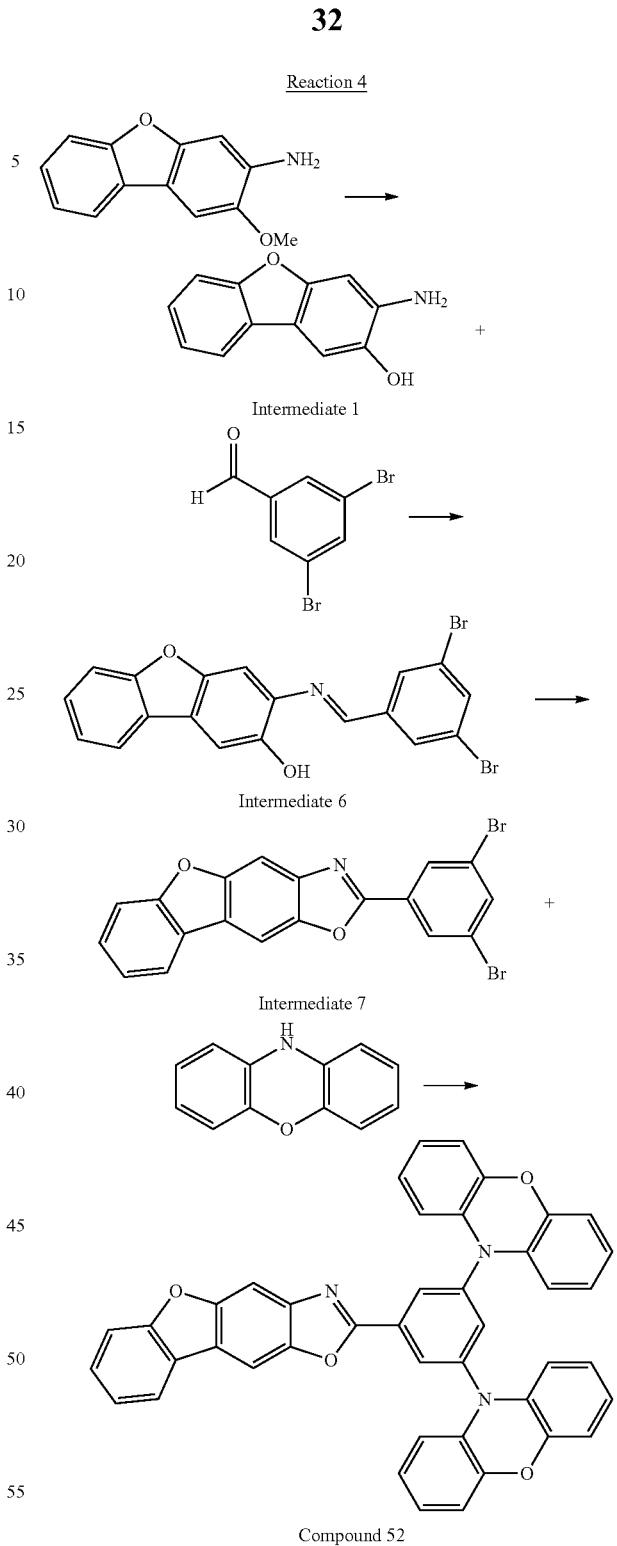

Synthesis of Intermediate 6

In a one-neck 2,000 ml flask, 31.5 g (158.1 mmol) of Intermediate 1, 62.5 g (237.2 mmol) of 3,5-dibromobenzaldehyde and 1,054 ml of ethanol were mixed and stirred at about 90° C. for about 4 hours. After finishing the reaction, the resultant product was cooled to room temperature. The solid thus precipitated was filtered while washing with ethanol. 42.1 g (yield: 60.0%) of a brown solid compound (Intermediate 6) was obtained.

Synthesis of Intermediate 7

To a one-neck 2,000 ml flask, 42.05 g (94.4 mmol) of Intermediate 6 and 765 ml of dichloromethane were added and stirred at room temperature. 31.3 g (137.78 mmol) of 2,3-dichloro-5,6-dicyano-p-benzoquinone (DDQ) was slowly added thereto and stirred at about 40° C. for about 3 hours. After finishing the reaction, the reaction product was passed through a celite pad using hot chloroform, and solvents were removed using distillation under a reduced pressure. The compound thus obtained was made into a slurry using 50 ml of chloroform and 500 ml of methanol to obtain 33.4 g (yield: 79.8%) of a beige solid compound (Intermediate 7).

Synthesis of Compound 52

In a one-neck 250 ml flask, 3.0 g (6.8 mmol) of Intermediate 7, 2.5 g (13.9 mmol) of phenoxazine, 0.4 g (0.68 mmol) of Pd(dba)$_2$, 0.4 g (1.0 mmol) of S-phos, 2.0 g (20.3 mmol) of NaOtBu and 45 ml of xylene were refluxed and stirred for about 30 minutes. After cooling to room temperature, methanol was added to solidify. After filtering, the solid thus obtained was dissolved in chloroform by heating and then separated by silica gel column chromatography (CHCl$_3$:Hex=1:4→2:1). To the product obtained by heating in chloroform and then sufficiently cooling, a small amount of acetone was added to solidify. The solid thus obtained was filtered to obtain 1.9 g (yield: 44.2%) of Compound 52 as a yellow solid. The measured value of the molecular weight of Compound 52 measured by FAB-MS was MS[M+H]$^+$=648.

(5) Synthesis of Compound 55

Compound 55 according to an embodiment may be synthesized, for example, by the steps (acts) of the following Reaction 5:

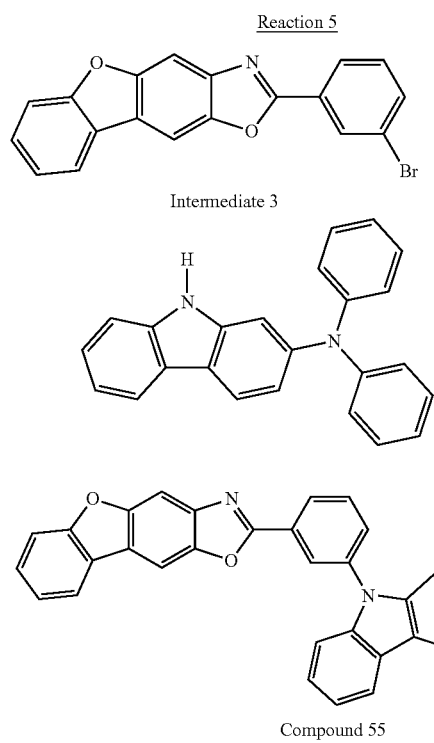

Compound 55

In a one-neck 250 ml flask, 1.6 g (4.5 mmol) of Intermediate 3, 3.0 g (9.0 mmol) of N,N-diphenyl-9H-carbazol-2-amine, 0.3 g (0.5 mmol) of Pd(dba)$_2$, 0.26 g (0.5 mmol, 50 wt % toluene solution) of P(t-Bu)$_3$, 1.5 g (15.8 mmol) of NaOtBu and 45 ml of xylene were refluxed and stirred for one day. After cooling at room temperature, impurities were removed through celite filtering. After completely removing solvents, the crude product was separated by silica gel column chromatography (MC:Hex=1:8→1:1). The product thus obtained was solidified (acetone:MeOH=2:1) and filtered to obtain 2.0 g (yield: 71.2%) of Compound 55 as a reddish brown solid. The measured value of the molecular weight of Compound 55 measured by FAB-MS was MS[M+H]$^+$=618.

(6) Synthesis of Compound 56

Compound 56 according to an embodiment may be synthesized, for example, by the steps (acts) of the following Reaction 6:

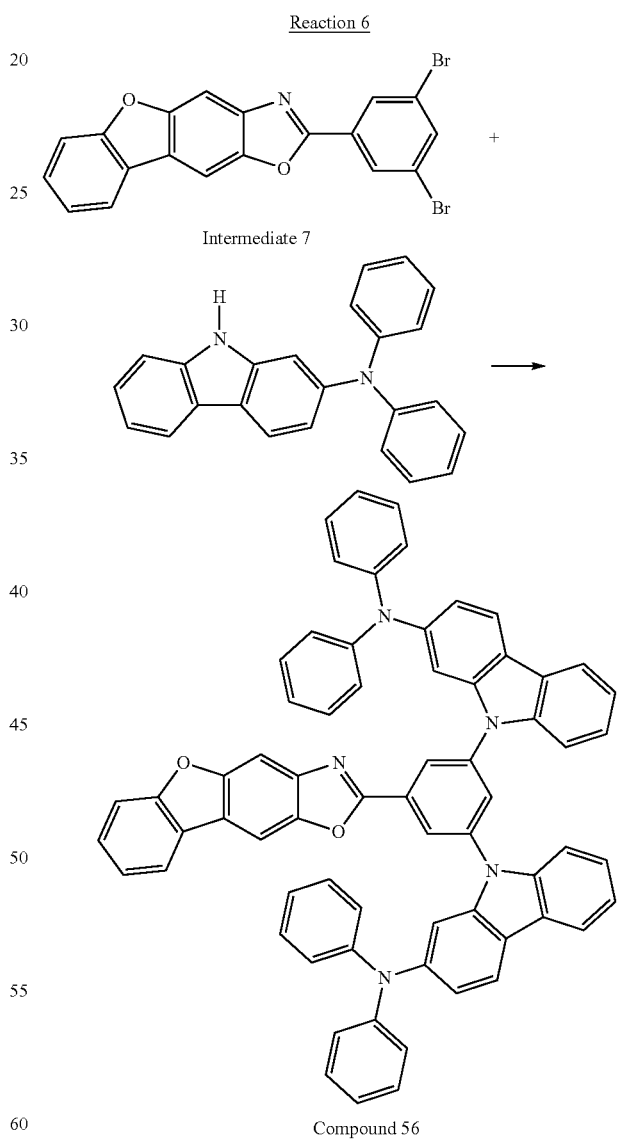

Compound 56

In a one-neck 250 ml flask, 2.0 g (4.5 mmol) of Intermediate 7, 3.0 g (9.0 mmol) of N,N-diphenyl-9H-carbazol-2-amine, 0.3 g (0.5 mmol) of Pd(dba)$_2$, 0.26 g (0.5 mmol, 50 wt % toluene solution) of P(t-Bu)$_3$, 1.5 g (15.8 mmol) of NaOtBu and 45 ml of xylene were refluxed and stirred for one day. After cooling at room temperature, impurities were removed through celite filtering. After completely removing solvents, the crude product was separated by silica gel column chromatography (MC:Hex=1:8→1:1). The product thus obtained was solidified (acetone:MeOH=2:1) and filtered to obtain 2.6 g (yield: 61.5%) of Compound 56 as a reddish brown solid. The measured value of the molecular weight of Compound 56 measured by FAB-MS was MS[M+H]$^+$=950.

(7) Synthesis of Compound 1

Compound 1 according to an embodiment may be synthesized, for example, by the steps (acts) of the following Reaction 7:

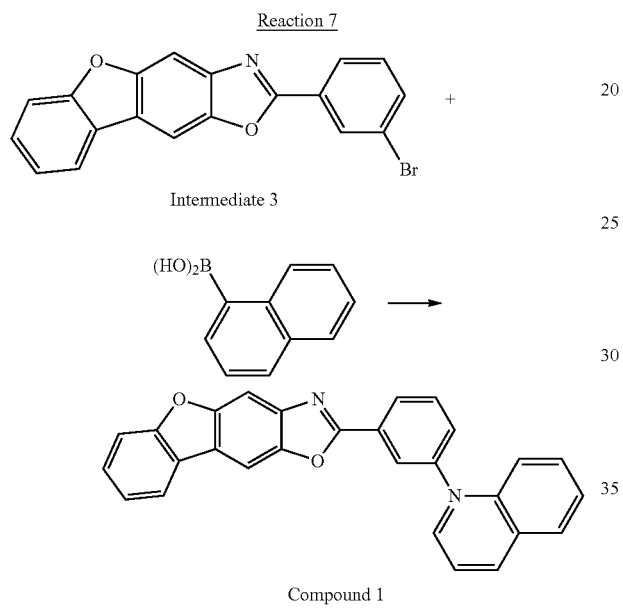

Compound 1

In a one-neck 250 ml flask, 1.6 g (4.5 mmol) of Intermediate 3, 1.0 g (6.0 mmol) of 1-naphthalen-1-ylboronic acid, and 100 ml of toluene were refluxed and stirred for one day using a Dean-Stark apparatus. Then, the resultant product was cooled, and solvents were completely removed. The crude product was separated by silica gel column chromatography (MC:Hex=1:4) to obtain 1.70 g (yield: 92.0%) of Compound 1 as a white solid. The measured value of the molecular weight of Compound 1 measured by FAB-MS was MS[M+H]$^+$=412.

(8) Synthesis of Compound 3

Compound 3 according to an embodiment may be synthesized, for example, by the steps (acts) of the following Reaction 8:

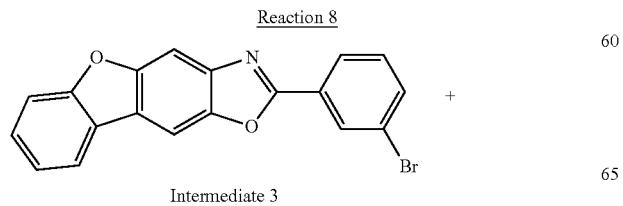

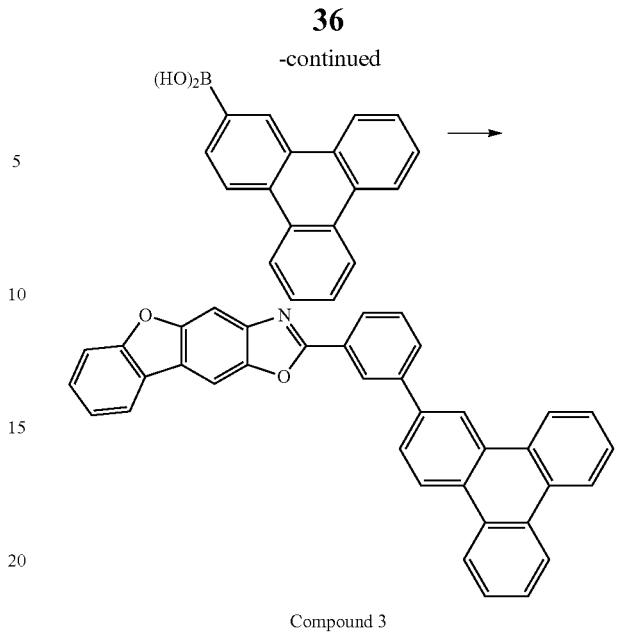

Compound 3

In a one-neck 250 ml flask, 1.6 g (4.5 mmol) of Intermediate 3, 1.6 g (6.0 mmol) of 2-triphenylen-1-ylboronic acid, and 100 ml of toluene were mixed and refluxed for one day using a Dean-Stark apparatus. Then, the resultant product was cooled, and solvents were completely removed. The crude product was separated by silica gel column chromatography (MC:Hex=1:4) to obtain 1.91 g (yield: 88.3%) of Compound 3 as a white solid. The measured value of the molecular weight of Compound 3 measured by FAB-MS was MS[M+H]$^+$=512.

2. Evaluation of Compounds

The fluorescence light-emitting properties of the synthesized Example Compounds of the present embodiments were evaluated. The evaluation of the light-emitting properties of Comparative Compounds was conducted together with the example Compounds. The compounds used for the evaluation are shown below.

(Example Compounds Used for Evaluating Light-Emitting Properties)

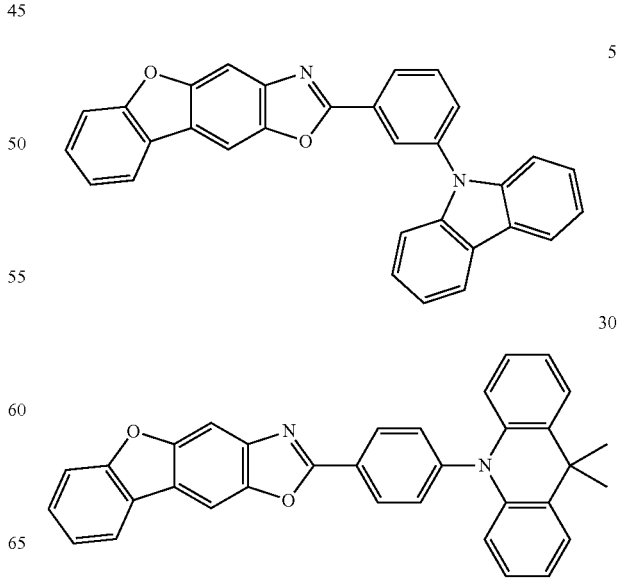

34

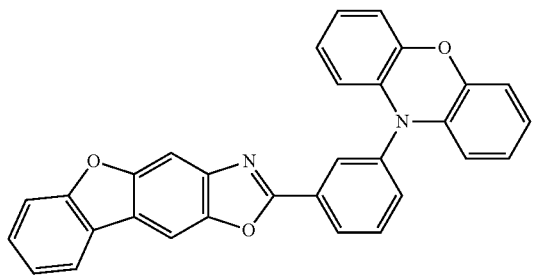

52

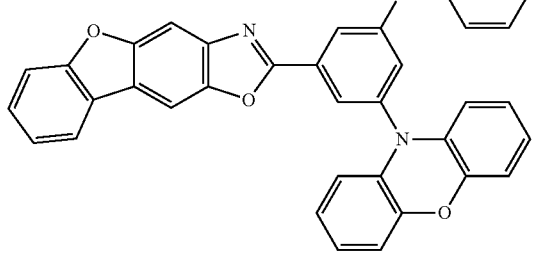

55

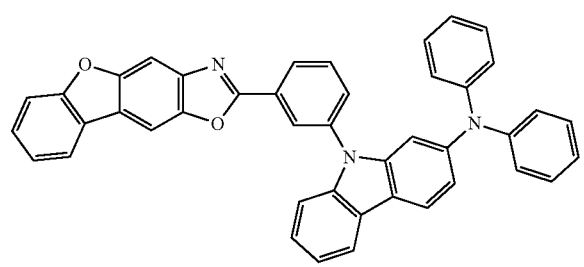

56

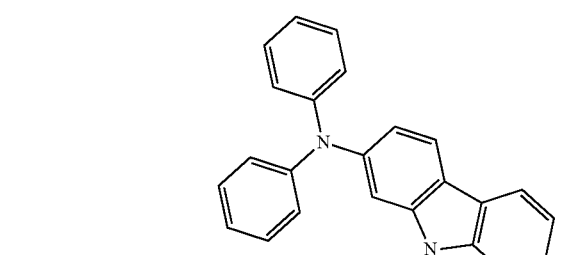

(Comparative Compounds Used for Evaluating Light-Emitting Properties)

C1

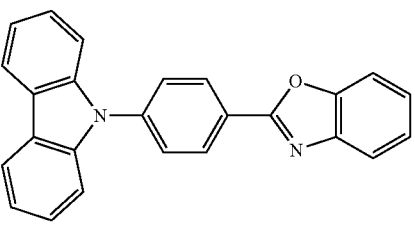

C2

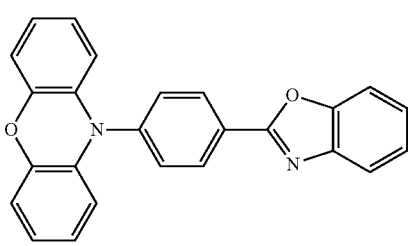

The $\Delta E_{ST}$ values and emission wavelengths of the Example Compounds of embodiments and Comparative Compounds were evaluated. The evaluation results of the properties are shown in Table 1. $E_{ST}$ corresponds to a difference between the lowest singlet excitation energy level (S1 level) and the lowest triplet excitation energy level (T1 level), and was calculated using a Gaussian calculation method (basis set B3LYP/6-31G*). In addition, the emission wavelengths of the Example Compounds and Comparative Compounds were confirmed using emission spectrum.

TABLE 1

| Division | $\Delta E_{ST}$ | Emission wavelength |
|---|---|---|
| Compound 5 | 0.35 eV | Blue |
| Compound 30 | 0.01 eV | Green |
| Compound 34 | 0.02 eV | Green |
| Compound 52 | 0.02 eV | Green |
| Compound 55 | 0.01 eV | Blue |
| Compound 56 | 0.01 eV | Green |
| Compound C1 | 0.57 eV | Blue |
| Compound C2 | 0.01 eV | Green |

Referring to the results of Table 1, the compounds of the present embodiments could be used as light-emitting materials emitting blue light or green light. In addition, Compounds 30, 34, 52, 55, 56, etc. have a small $\Delta E_{ST}$ value of about 0.02 eV or less and are believed can be used as materials for emitting delayed fluorescence.

3. Manufacture and Evaluation of Organic Electroluminescence Device 3-1. Example A of Organic Electroluminescence Devices Including the Compounds of Embodiments Organic electroluminescence devices of embodiments including the compounds of embodiments as the host materials of an emission layer were manufactured by a method described below.

Manufacture of Organic Electroluminescence Device

A glass substrate on which ITO was patterned was washed using ultrapure water and ultrasonic waves, exposed to UV for about 30 minutes and treated with ozone. Then, HT1 was deposited to a thickness of about 1,200 Å, and HT2 was deposited to a thickness of about 100 Å to form a hole transport region.

Then, the Example Compound or the Comparative Compound was co-deposited with 4CzIPN in a ratio of 80:20 to form an emission layer into a thickness of about 400 Å. That is, the emission layer of each Example formed by the co-deposition was obtained by mixing and depositing a corresponding Example Compound with 4CzIPN, and the emission layer of each Comparative Example was obtained by mixing and depositing a corresponding Comparative Compound with 4CzIPN.

Then, ET and Liq were mixed in a ratio of 5:5 and deposited on the emission layer to form a layer having a thickness of about 300 Å, and a layer of a thickness of about 10 Å was formed using Liq, thus forming an electron transport region. Then, a second electrode was formed using Mg:Ag (10:1) to a thickness of about 100 Å.

In the Examples and Comparative Examples, the hole transport region, the emission layer, the electron transport region and the second electrode were formed using a vacuum deposition apparatus. The materials for the hole transport region, the material for the electron transport region and the dopant material used for the manufacture of the organic electroluminescence devices are shown below.

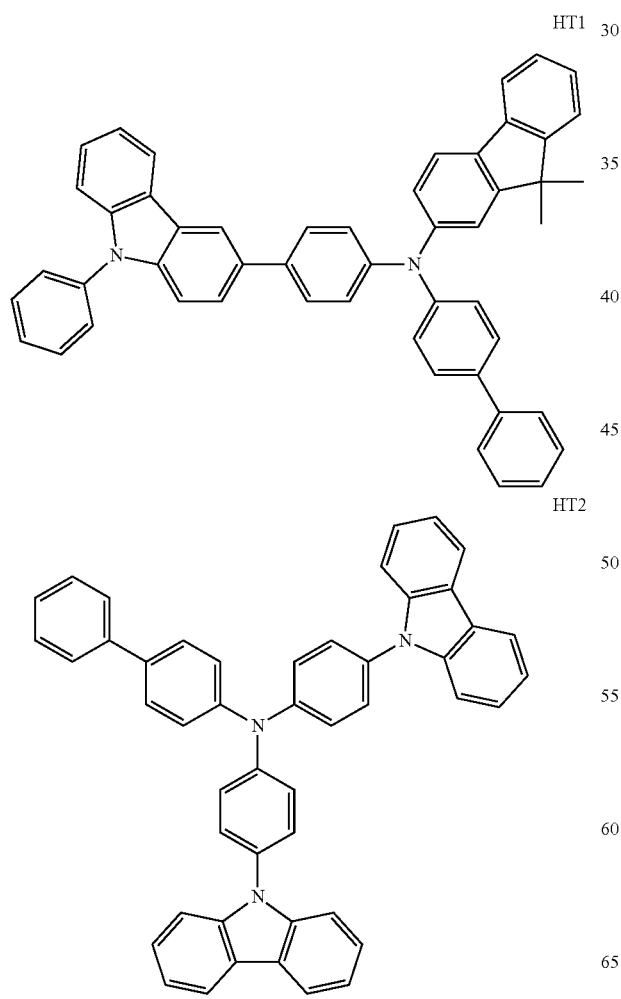

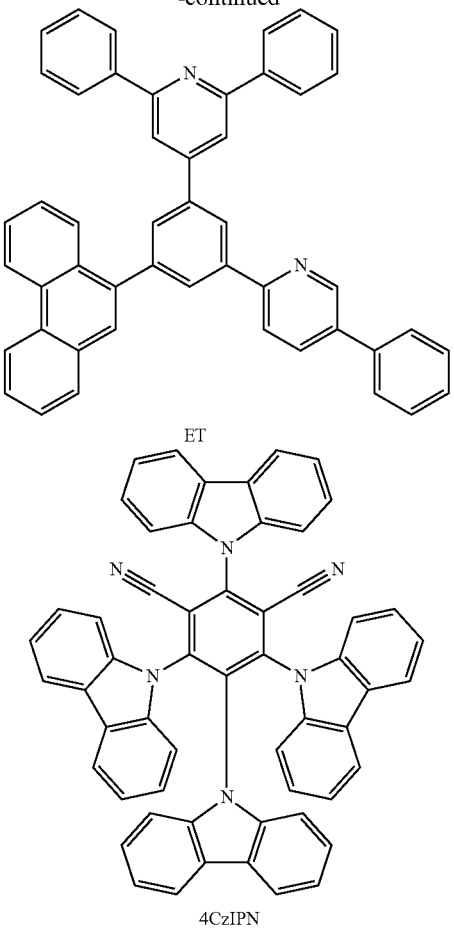

Evaluation of Properties of Organic Electroluminescence Device

In Table 2, the efficiency, life, and emission color of the organic electroluminescence devices thus manufactured are compared. In the evaluation results of the properties of the Examples and Comparative Example shown in Table 2, the efficiency represents a current efficiency value with respect to a current density of 10 mA/cm$^2$. In addition, in the evaluation results of the emission properties of the organic electroluminescence devices, the efficiency and life of the Examples were compared as relative values when the efficiency and life of Comparative Example 1-1 were set to 100%.

In Example 1-1 and Example 1-2, Compound 1 and Compound 3 were used, respectively, as the host materials of the emission layer. In Comparative Example 1-1, a known host material, mCBP, was used as the host material of the emission layer.

TABLE 2

| Division | Host | Dopant | Efficiency | Life | Emission color |
|---|---|---|---|---|---|
| Example 1-1 | Compound 1 | 4CzIPN | 95% | 140% | Green |
| Example 1-2 | Compound 3 | 4CzIPN | 105% | 155% | Green |
| Comparative Example 1-1 | mCBP | 4CzIPN | 100% | 100% | Green |

Referring to the results of Table 2, it could be confirmed that Example 1-1, Example 1-2 and Comparative Example 1-1 all emitted light in a green wavelength region. When compared with Comparative Example 1-1, it could be found that Example 1-1 showed somewhat decreased efficiency but improved life characteristics. In addition, when compared with Comparative Example 1-1, it could be found that Example 1-2 showed improved efficiency and improved life characteristics.

Accordingly, it could be found that the compound according to an embodiment may be used as the host material of an emission layer emitting light in a green wavelength region, and may show excellent (or improved) life characteristics when compared with the comparable host material.

3-2. Example B of Organic Electroluminescence Devices Including the Compounds of Embodiments Organic electroluminescence devices of embodiments including the compounds of embodiments as the dopant materials of an emission layer were manufactured by a method described below.

Manufacture of Organic Electroluminescence Device

A glass substrate on which ITO was patterned was washed using ultrapure water and ultrasonic waves, exposed to UV for about 30 minutes and treated with ozone. Then, HT1 was deposited to a thickness of about 1,200 Å, and HT2 was deposited to a thickness of about 100 Å to form a hole transport region.

Then, the Example Compound or the Comparative Compound was co-deposited with mCBP in a ratio of 20:80 to form an emission layer into a thickness of about 400 Å. That is, the emission layer of each Example formed by the co-deposition was obtained by mixing and depositing a corresponding Example Compound with mCBP, and the emission layer of each Comparative Example was obtained by mixing and depositing a corresponding Comparative Compound with mCBP.

Then, ET and Liq were mixed in a ratio of 5:5 and deposited on the emission layer to form a layer having a thickness of about 300 Å, and a layer of a thickness of about 10 Å was formed using Liq, thus forming an electron transport region. Then, a second electrode was formed using Mg:Ag (10:1) to a thickness of about 100 Å.

In the Examples and Comparative Examples, the hole transport region, the emission layer, the electron transport region and the second electrode were formed using a vacuum deposition apparatus.

Evaluation of Properties of Organic Electroluminescence Device

In Table 3, the efficiency, life, and emission color of the organic electroluminescence devices thus manufactured are compared. In the evaluation results of the properties of the Examples and Comparative Examples shown in Table 3, the efficiency represents a current efficiency value with respect to a current density of 10 mA/cm$^2$. In addition, in the evaluation results of the properties of the organic electroluminescence devices, the efficiency and life of the Examples were compared as relative values when the efficiency and life of Comparative Example 2-1 or Comparative Example 3-1 were set to 100%.

In the evaluation results shown in Table 3 below, Example 2-1, Example 2-2, and Comparative Example 2-1 show evaluation results of the organic electroluminescence devices emitting light in a blue wavelength region, and Example 3-1 to Example 3-4 and Comparative Example 3-1 show evaluation results of the organic electroluminescence devices emitting light in a green wavelength region. In Example 2-1, Example 2-2, Comparative Example 2-1, Example 3-1 to Example 3-4 and Comparative Example 3-1, a known host material, mCBP, was used as the host material of the emission layer.

TABLE 3

| Division | Host | Dopant | Efficiency | Life | Emission color |
|---|---|---|---|---|---|
| Example 2-1 | mCBP | Compound 5 | 130% | 130% | Blue |
| Example 2-2 | mCBP | Compound 55 | 135% | 130% | Blue |
| Comparative Example 2-1 | mCBP | Comparative Compound C1 | 100% | 100% | Blue |
| Example 3-1 | mCBP | Compound 30 | 110% | 135% | Green |
| Example 3-2 | mCBP | Compound 34 | 115% | 140% | Green |
| Example 3-3 | mCBP | Compound 52 | 115% | 125% | Green |
| Example 3-4 | mCBP | Compound 56 | 125% | 180% | Green |
| Comparative Example 3-1 | mCBP | Comparative Compound C2 | 100% | 100% | Green |

Referring to the results of Table 3, it could be confirmed that the Examples correspond to organic electroluminescence devices emitting blue light or green light, and the compounds according to embodiments could be used as a blue dopant emitting blue light or a green dopant emitting green light.

In addition, referring to the results of Table 3, when compared with Comparative Example 2-1, Example 2-1 and Example 2-2 showed improved efficiency properties and life characteristics, and when compared with Comparative Example 3-1, Example 3-1 to Example 3-4 showed improved efficiency properties and excellent life characteristics.

Accordingly, referring to the evaluation results of Table 3, it could be confirmed that the compounds according to embodiments were used as the dopant materials of the emission layer of organic electroluminescence devices to emit blue light or green light. In addition, it could be found that when compared with the Comparative Compounds, the compounds of the present embodiments included a condensed structure of benzofuran and benzoxazole, and if used as the dopant material of an emission layer, the efficiency and life characteristics of the organic electroluminescence device could be improved.

The compound of an embodiment has a novel compound structure including a condensed ring of benzofuran and benzoxazole as an electron acceptor, and is used as a material for an emission layer to contribute to the increase of the efficiency and long-life characteristics of an organic electroluminescence device. In addition, the organic electroluminescence device of an embodiment, including the compound of an embodiment in an emission layer may show excellent emission properties and excellent life characteristics in a green emission wavelength region or a blue emission wavelength region.

The organic electroluminescence device of an embodiment may show improved device characteristics including high efficiency in a green wavelength region or a blue wavelength region and long life.

The compound of an embodiment may be included in the emission layer of an organic electroluminescence device and may contribute to the improvement of life characteristics and the increase of efficiency of the organic electroluminescence device.

As used herein, the terms "use," "using," and "used" may be considered synonymous with the terms "utilize," "utilizing," and "utilized," respectively.

In addition, the terms "substantially," "about," and similar terms are used as terms of approximation and not as terms of degree, and are intended to account for the inherent deviations in measured or calculated values that would be recognized by those of ordinary skill in the art.

Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Although the example embodiments of the present disclosure have been described, it is understood that the present disclosure should not be limited to these example embodiments, but that various changes and modifications can be made by one of ordinary skill in the art within the spirit and scope of the present disclosure as hereinafter claimed by the appended claims and their equivalents.

1
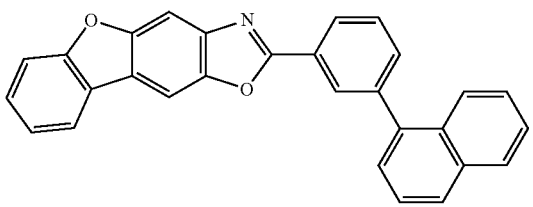

2
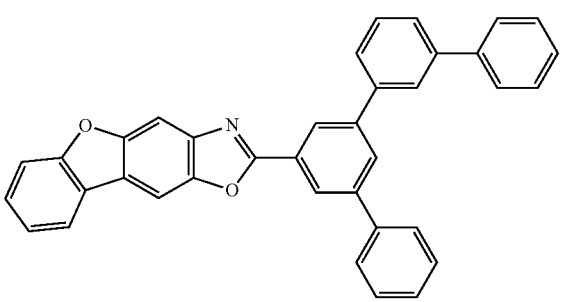

4
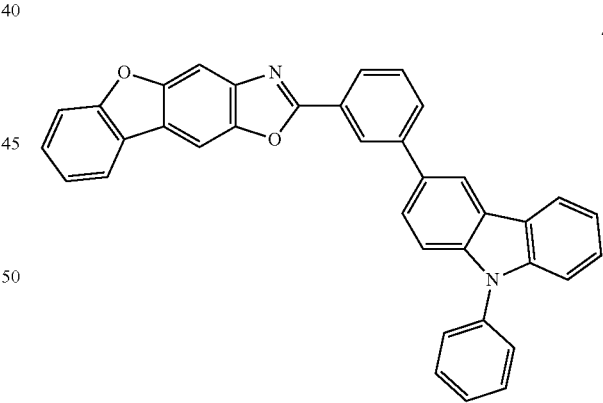

5

6
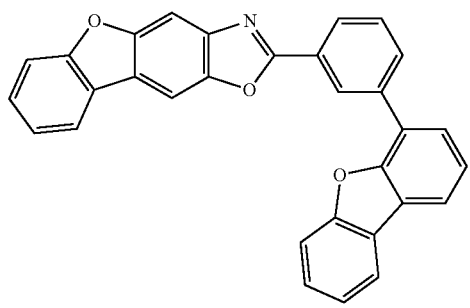
7
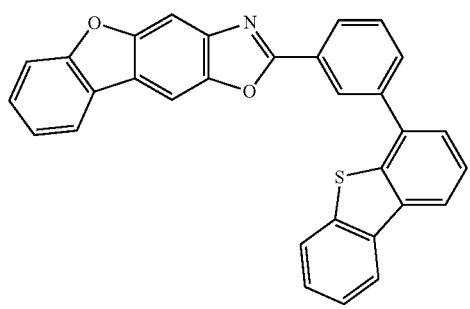
8
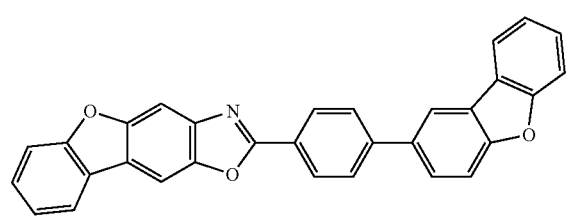
9
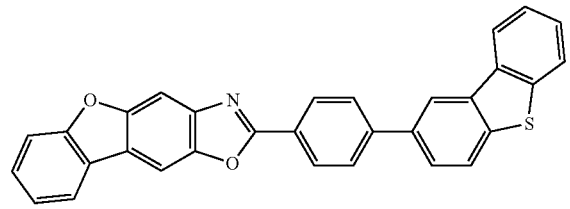
10
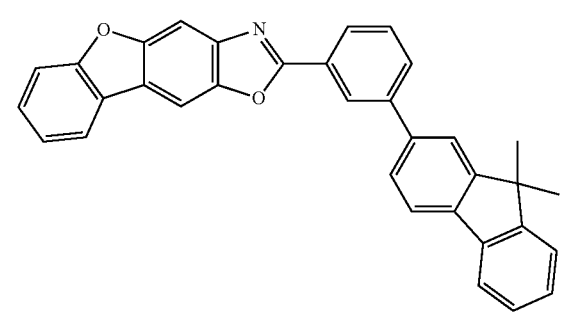
11
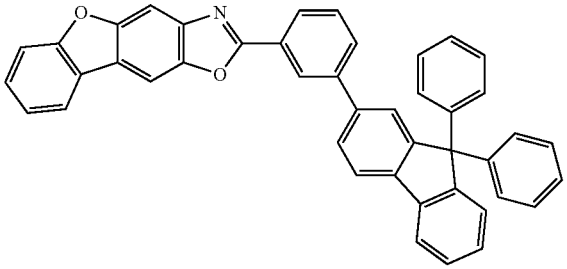
12
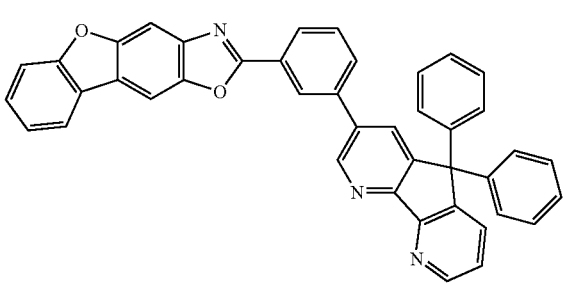
13
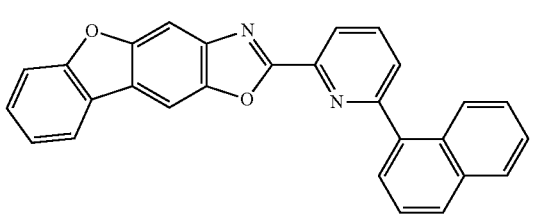
14
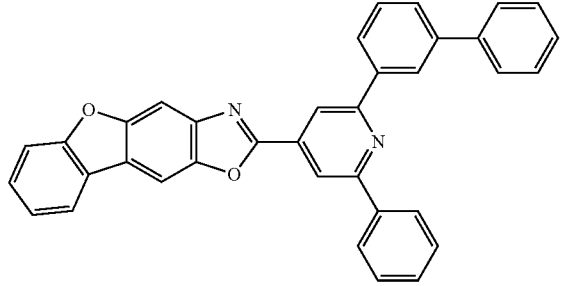
16
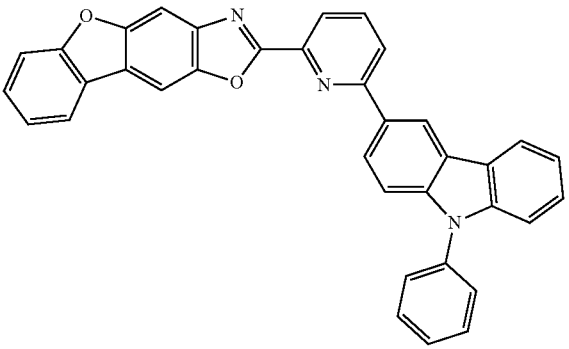

17
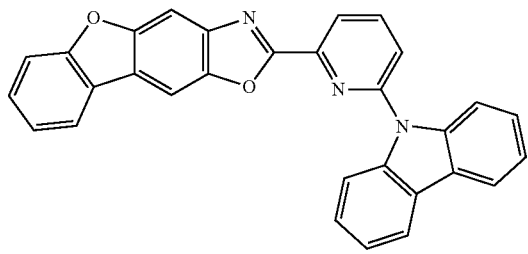
18
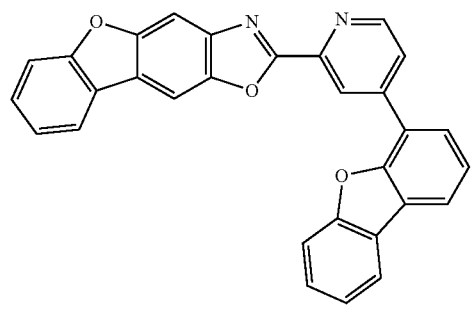
25
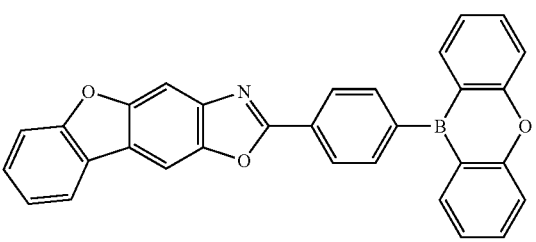
26
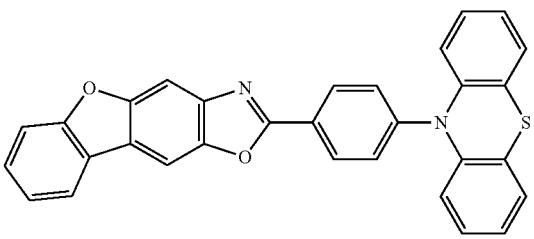
27
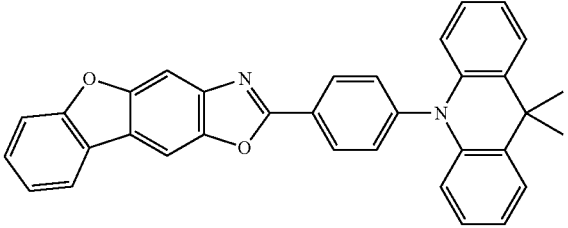
28
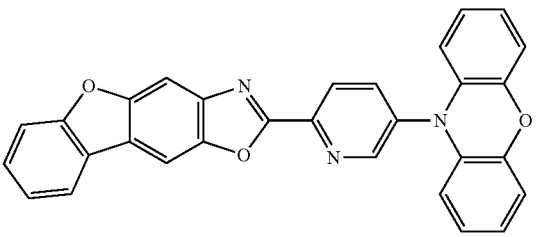
29
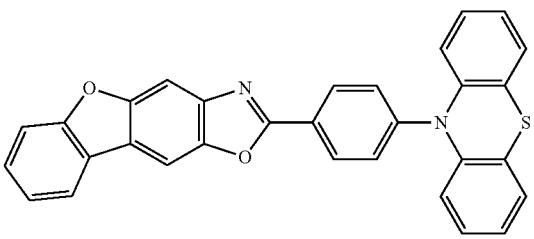
30
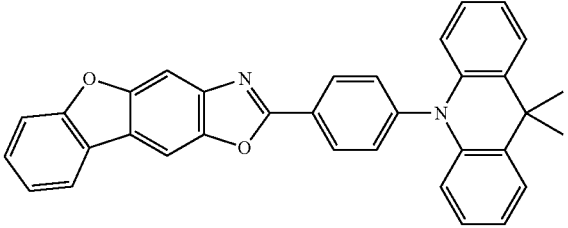
31
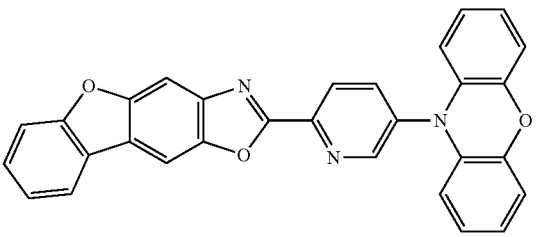
32
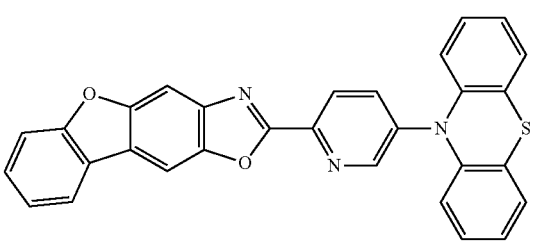
33
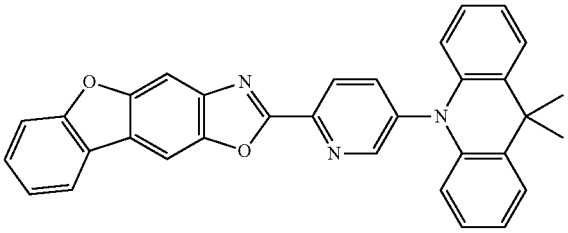
34
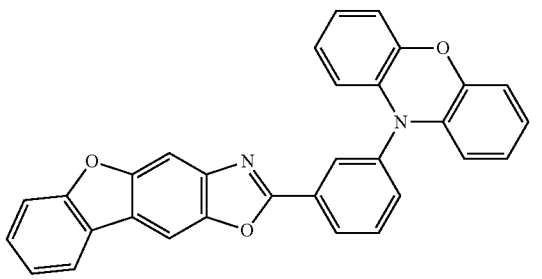

35
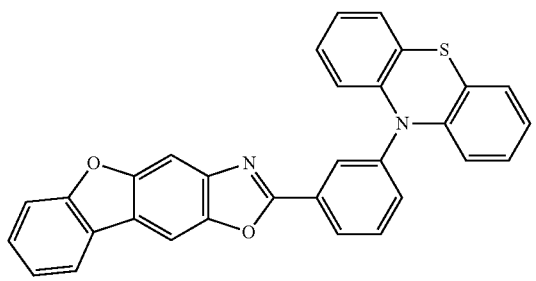
36
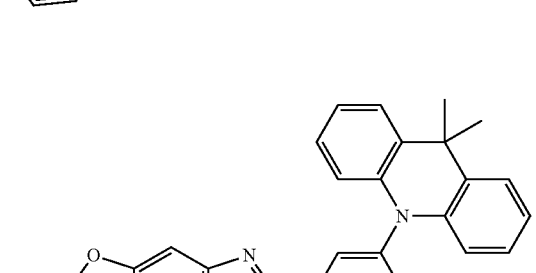
37
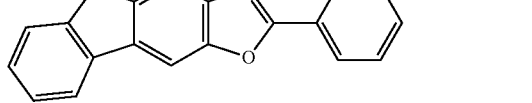
38
39
40
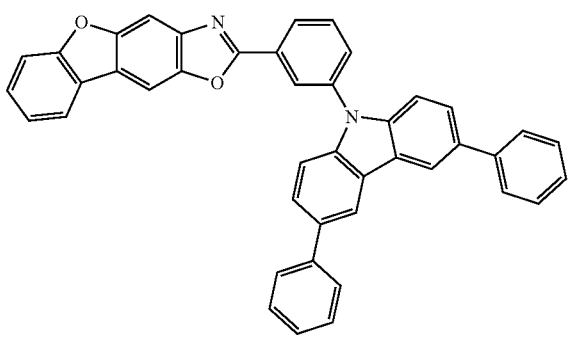
41
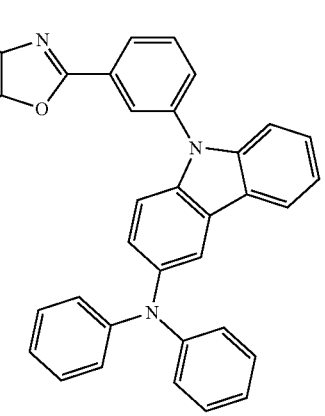
42
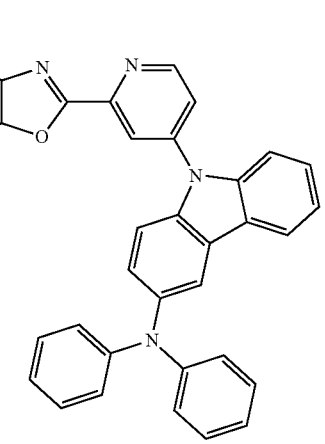
43
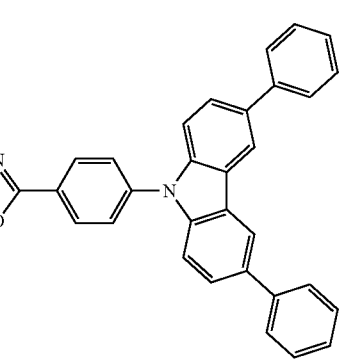

44
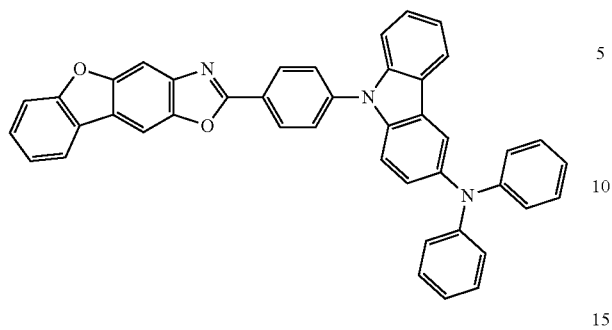
45
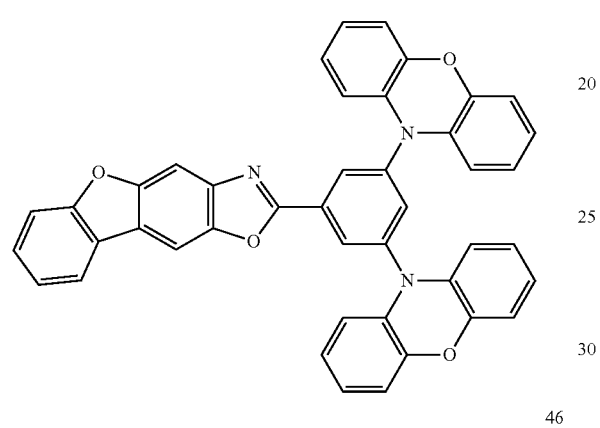
46
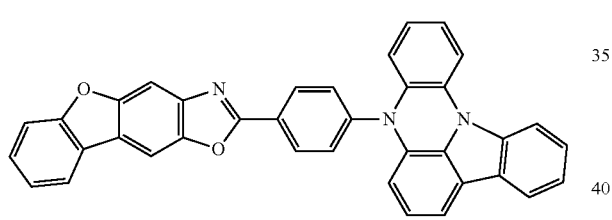
47
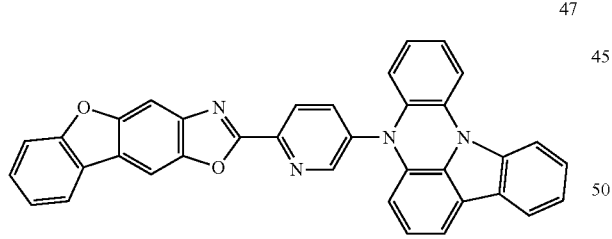
48
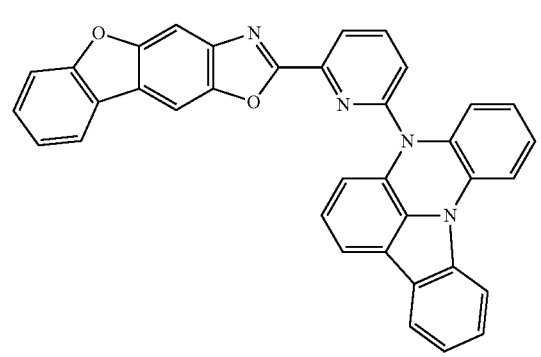
52
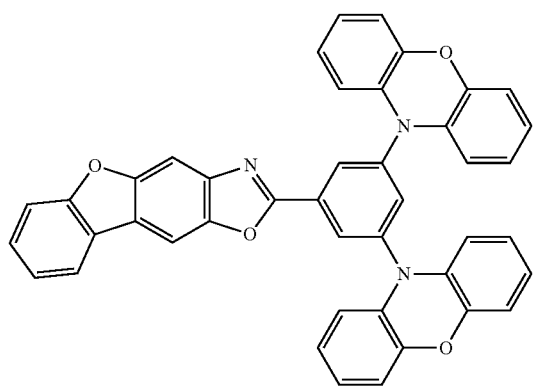
53
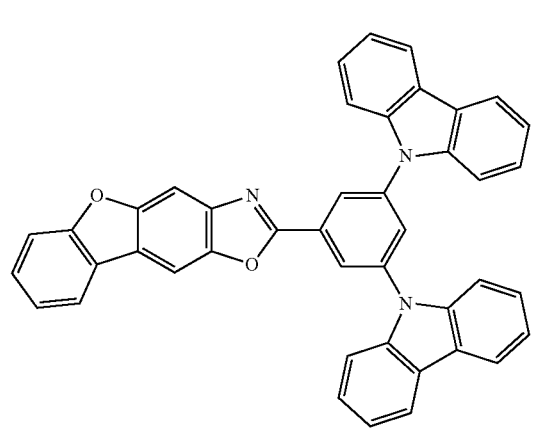
54
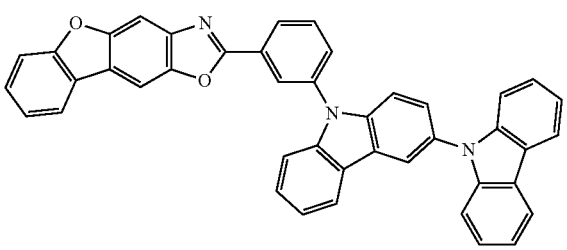
55
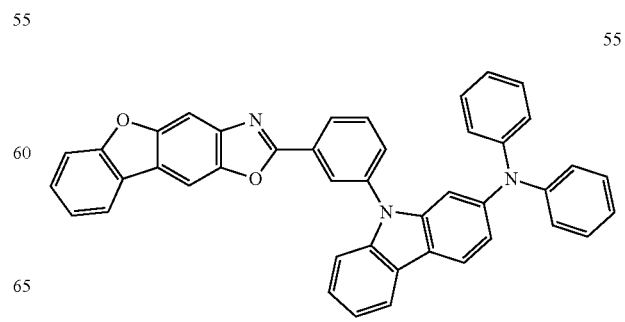

-continued
56
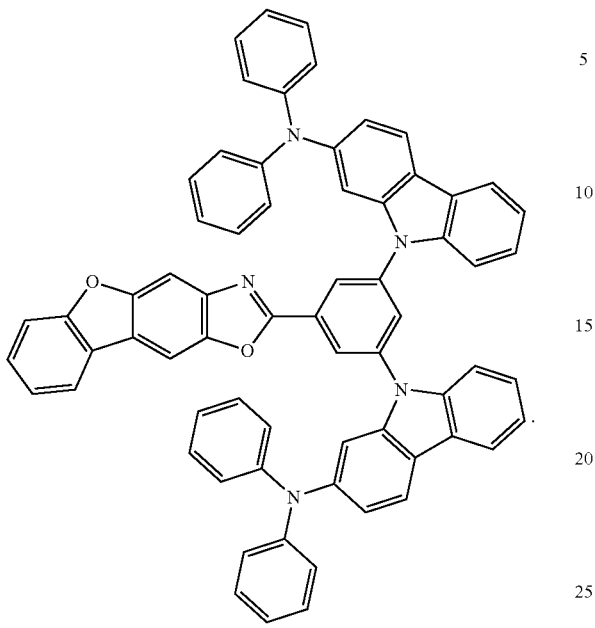

What is claimed is:

1. An organic electroluminescence device, comprising:
   a first electrode;
   a second electrode on the first electrode; and
   an emission layer between the first electrode and the second electrode, the emission layer comprising a compound represented by Formula 1:

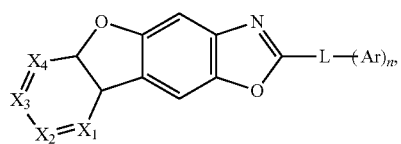

Formula 1 in Formula 1,
$X_1$ to $X_4$ are each independently $CR_a$,
L is a substituted or unsubstituted arylene group of 6 to 30 carbon atoms for forming a ring, or a substituted or unsubstituted heteroarylene group of 2 to 30 carbon atoms for forming a ring,
"n" is 1 or 2,
Ar is a substituted or unsubstituted aryl group of 6 to 15 carbon atoms for forming a ring, or represented by Formula 2:

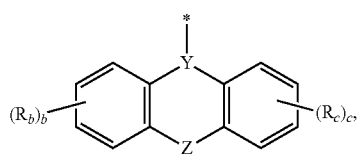

Formula 2 in Formula 2,
Y is N or B,
Z is a direct linkage, O, S, $NR_d$, or $CR_eR_f$,
"b" and "c" are each independently an integer of 0 to 4, and $R_b$ to $R_f$ are each independently a hydrogen atom, a deuterium atom, a halogen atom, a cyano group, a substituted or unsubstituted silyl group, a substituted or unsubstituted amine group, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, and/or combined with an adjacent group to form a ring, and $R_a$ is a hydrogen atom, a deuterium atom, a halogen atom, a cyano group, a substituted or unsubstituted silyl group, a substituted or unsubstituted amine group, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, and/or combined with an adjacent group to form a ring.

2. The organic electroluminescence device of claim 1, wherein L is a substituted or unsubstituted phenylene group, or a substituted or unsubstituted pyridylene group.

3. The organic electroluminescence device of claim 1, wherein Formula 2 is represented by Formula 2-1 or Formula 2-2:

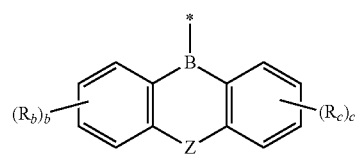

Formula 2-1

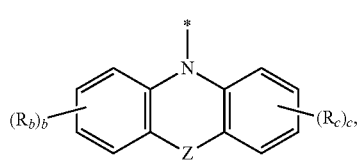

Formula 2-2 in Formula 2-1 and Formula 2-2, Z, $R_b$, $R_c$, "b", and "c" are the same as defined in Formula 2.

4. The organic electroluminescence device of claim 3, wherein Formula 2-2 is represented by any one selected from among Formula 2-2A to Formula 2-2E:

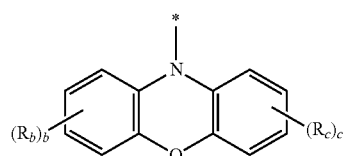

Formula 2-2A

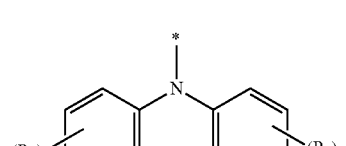

Formula 2-2B

-continued

Formula 2-2C

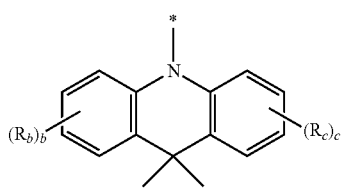

Formula 2-2D

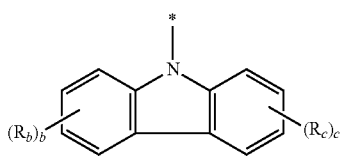

Formula 2-2E

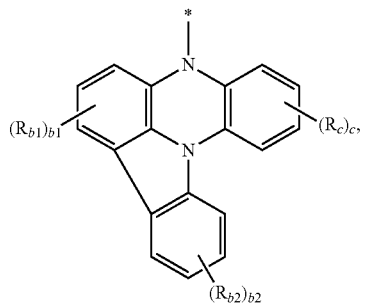

in Formula 2-2E,

"b1" is an integer of 0 to 3, "b2" is an integer of 0 to 4, and $R_{b1}$ and $R_{b2}$ are each independently a hydrogen atom, a deuterium atom, a halogen atom, a cyano group, a substituted or unsubstituted silyl group, a substituted or unsubstituted amine group, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, and/or combined with an adjacent group to form a ring, and in Formula 2-2A to Formula 2-2E, $R_b$, $R_c$, "b", and "c" are the same as defined in Formula 2.

5. The organic electroluminescence device of claim 1, wherein the emission layer comprises a host and a dopant, and the host comprises the compound.

6. The organic electroluminescence device of claim 1, wherein the emission layer is to emit delayed fluorescence, and the compound is a delayed fluorescence dopant.

7. The organic electroluminescence device of claim 1, wherein the emission layer is to emit light having a central wavelength of about 500 nm to about 550 nm, or light having a central wavelength of about 420 nm to about 470 nm.

8. An organic electroluminescence device, comprising:

a first electrode;

a second electrode on the first electrode; and an emission layer between the first electrode and the second electrode, wherein the emission layer comprises at least one selected from among compounds in Compound Group 1 as a light-emitting dopant:

Compound Group 1

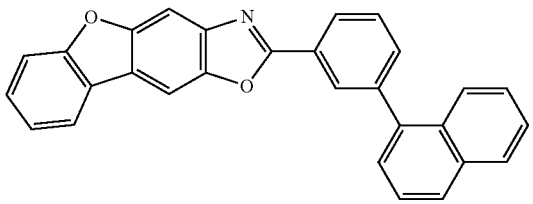
1

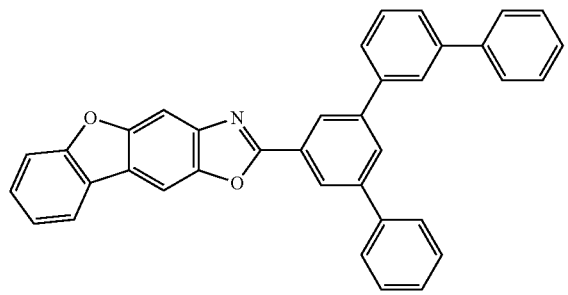
2

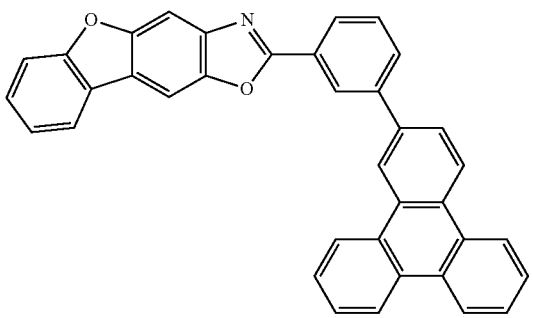
3

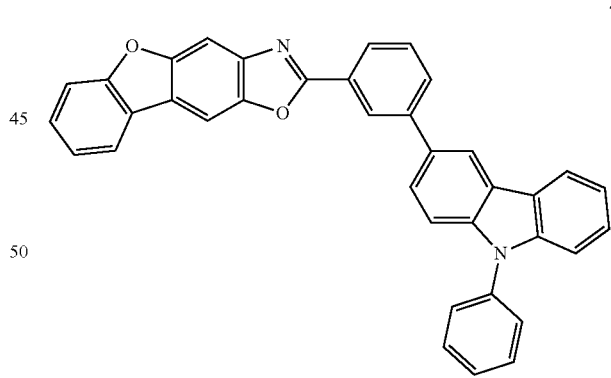
4

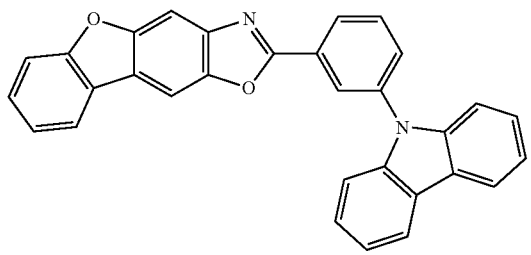
5

47
-continued
6
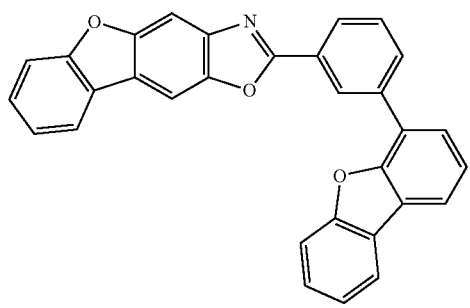
7
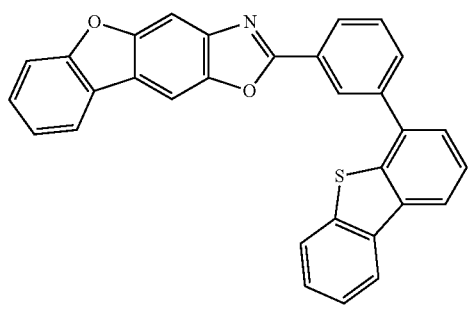
8
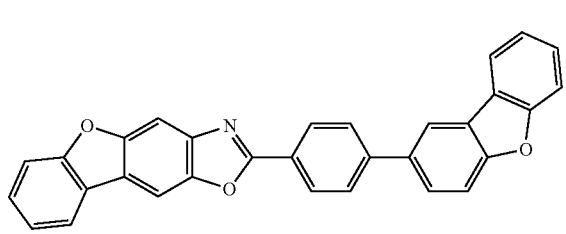
9
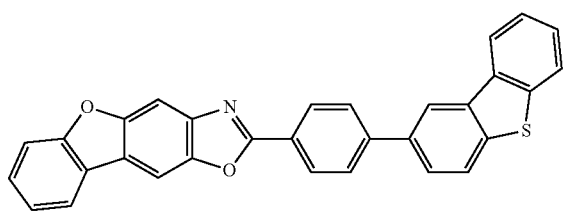
10
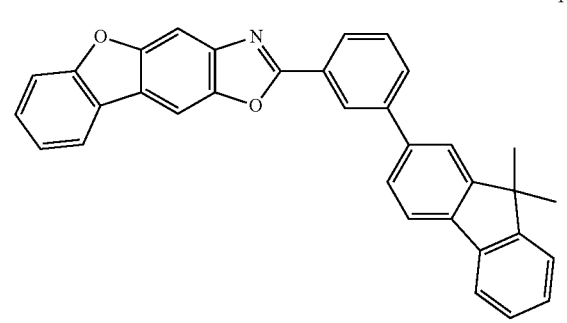
48
-continued
11
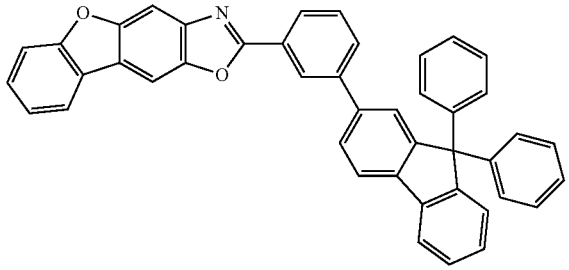
12
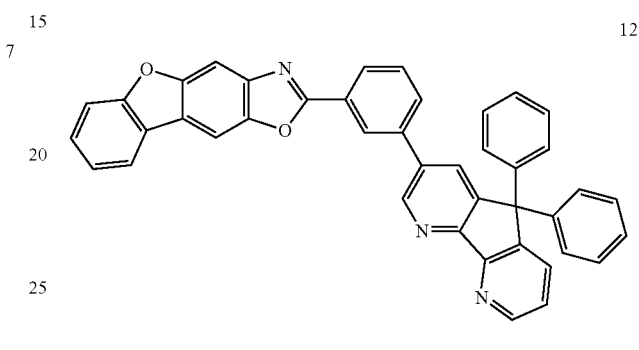
13
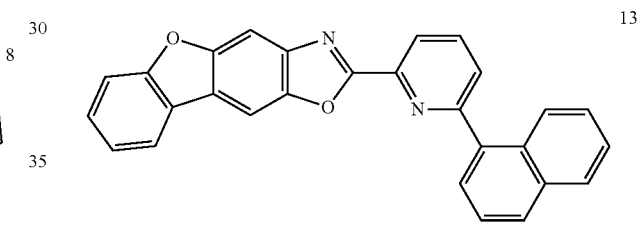
14
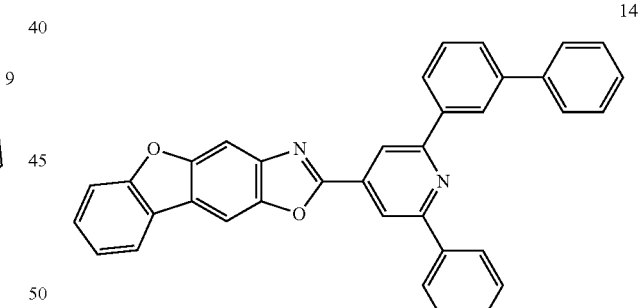
15
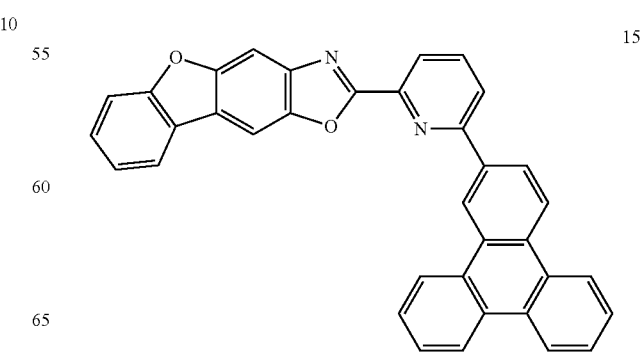

16
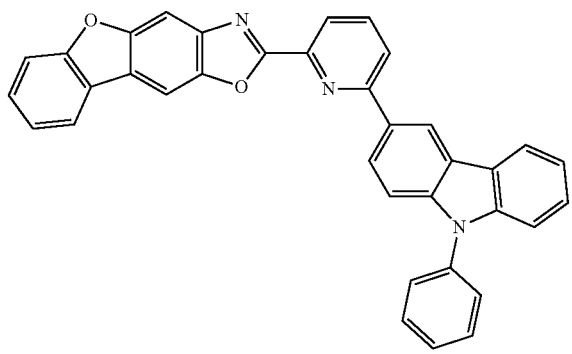
17
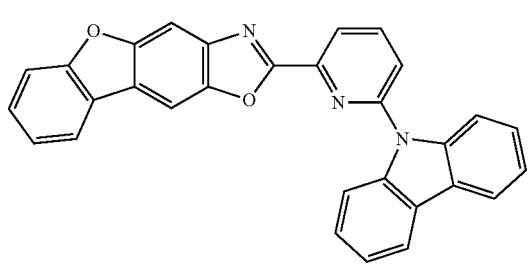
18
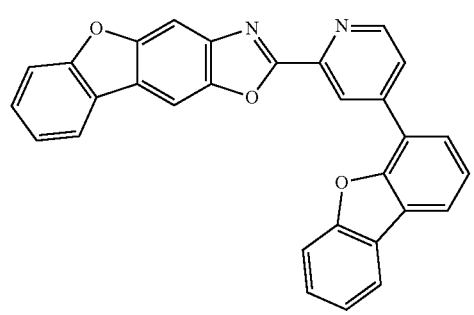
25
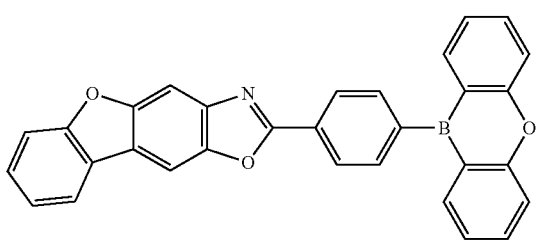
26
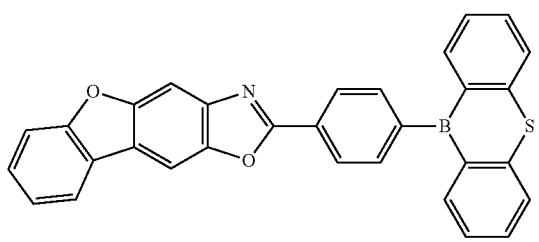
27
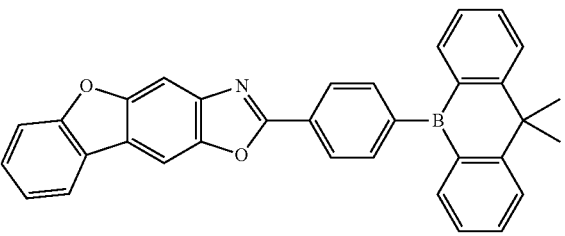
28
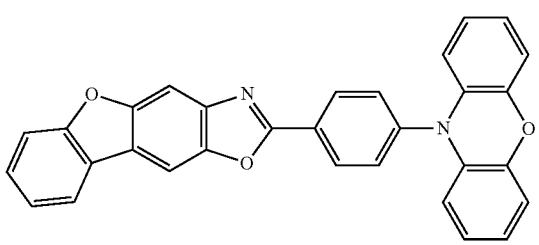
29
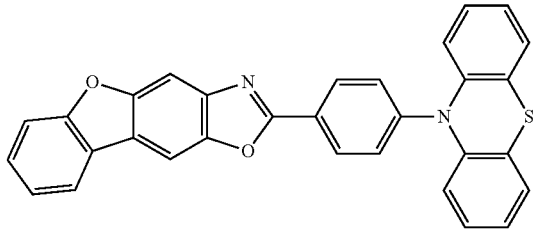
30
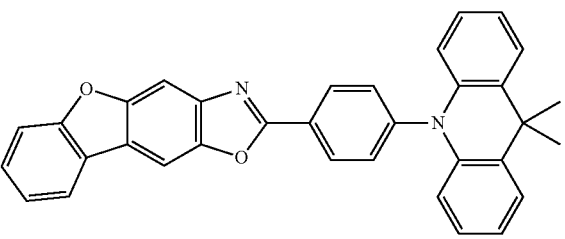
31
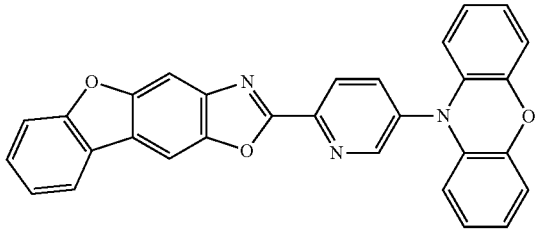
32
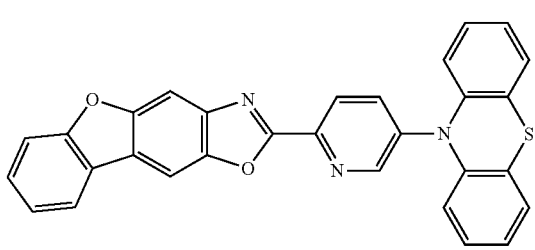

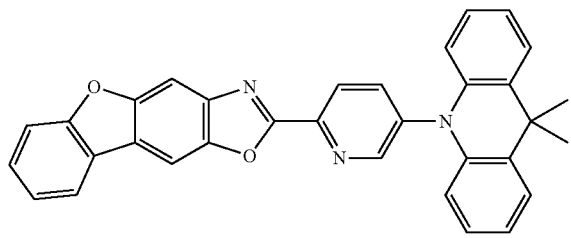
33
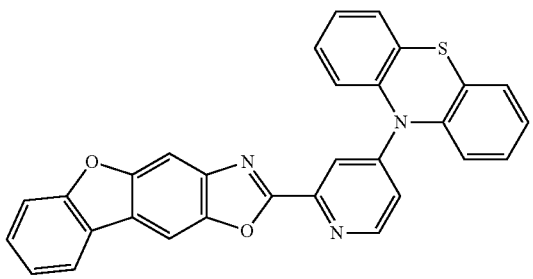
38
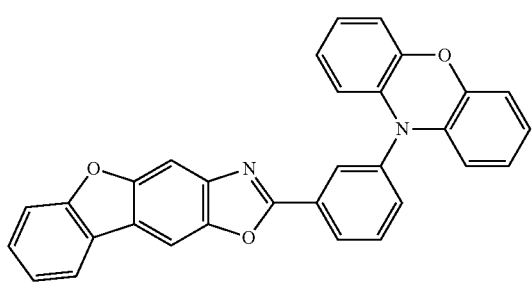
34
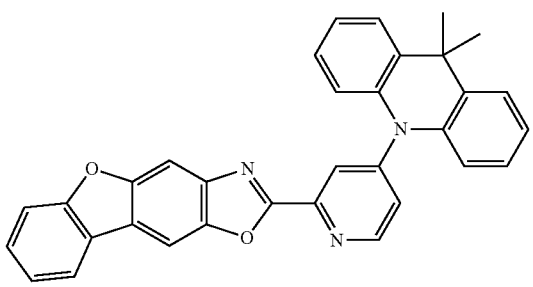
39
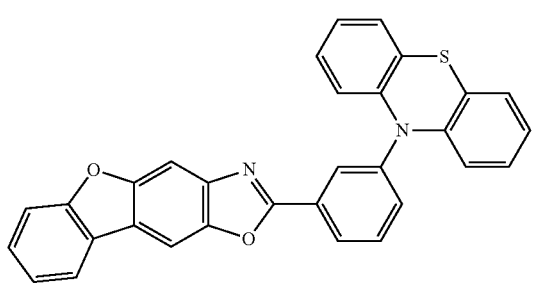
35
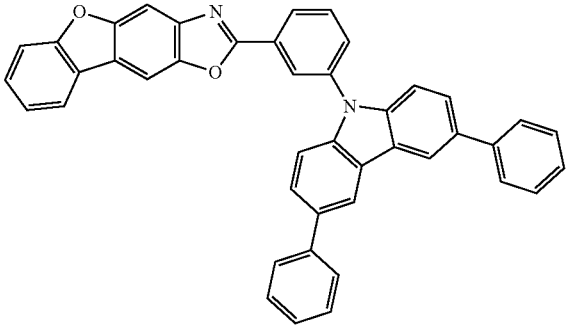
40
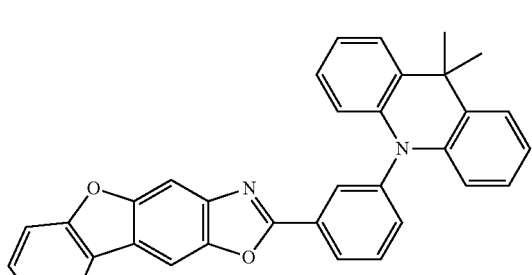
36
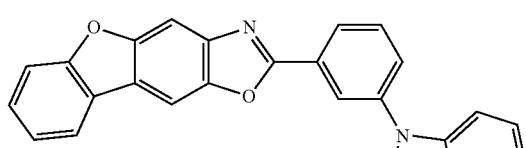
41
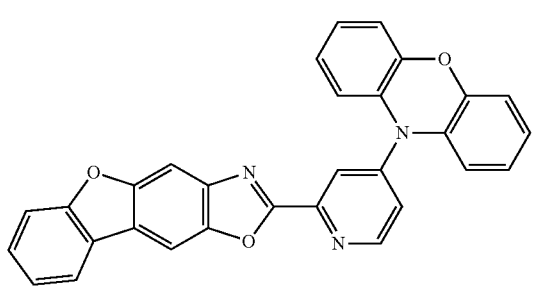
37
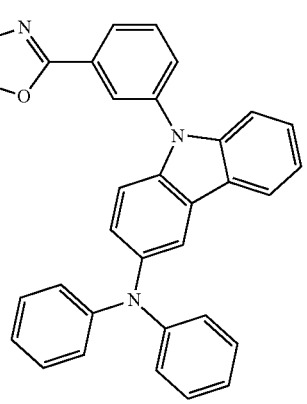

53
-continued
42
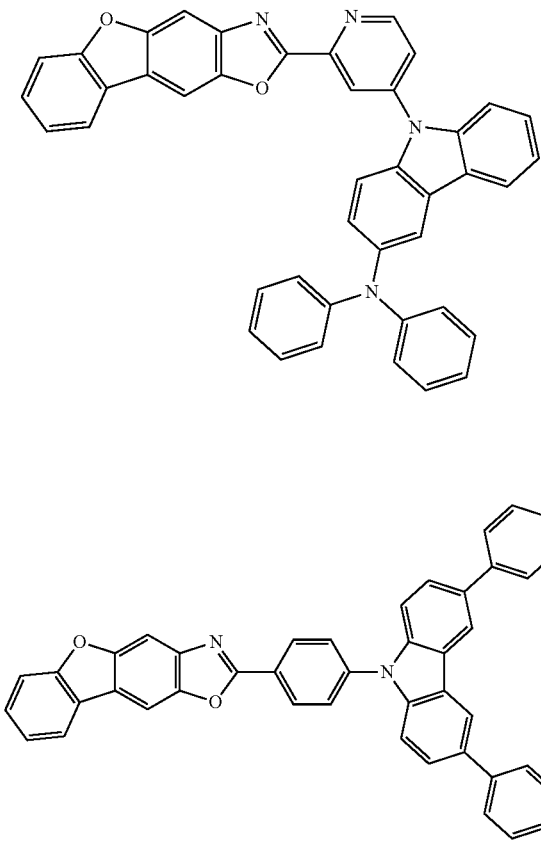
43
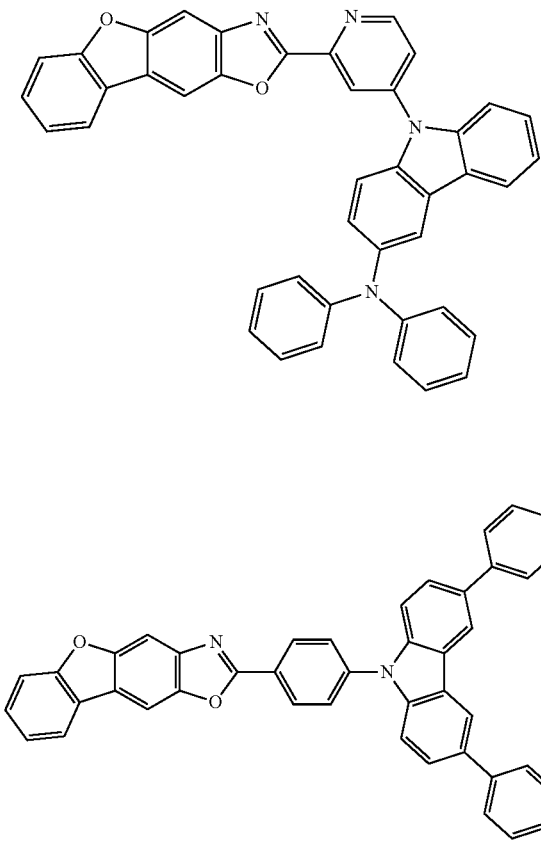
44
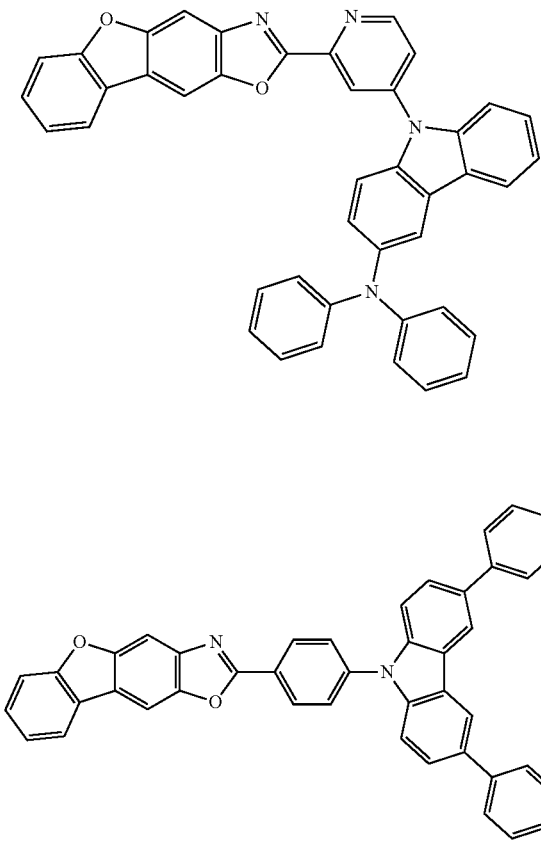
45
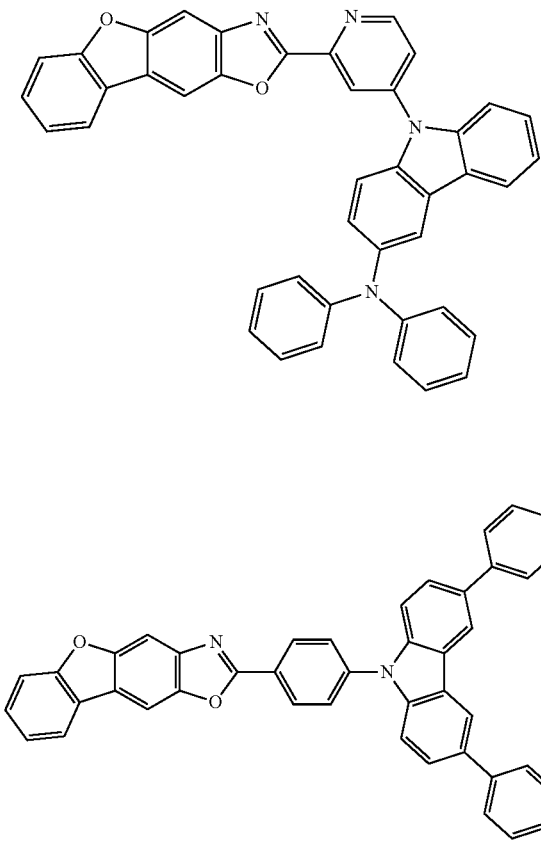
54
-continued
46
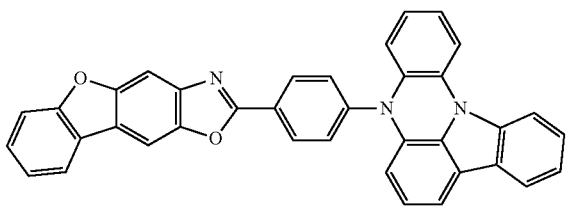
47
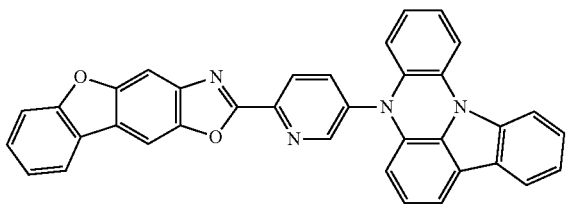
48
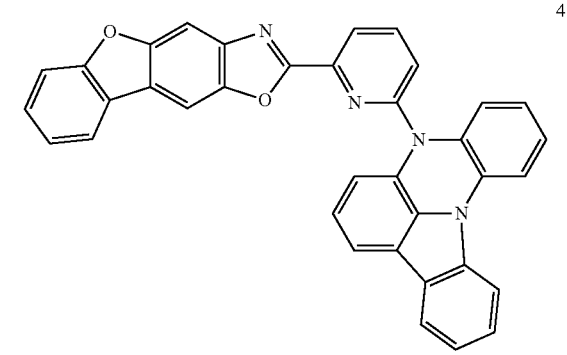
52
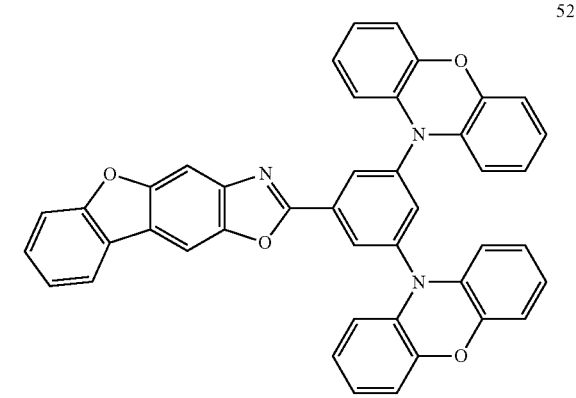
53
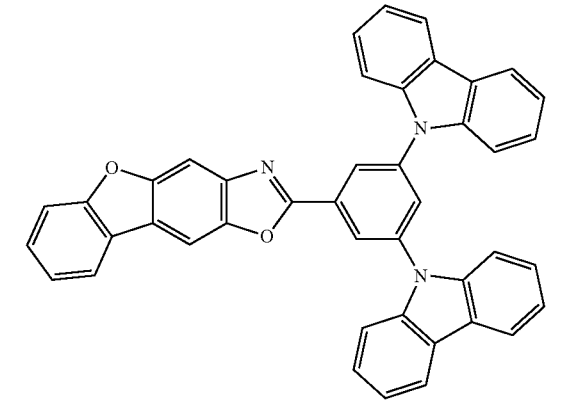

-continued

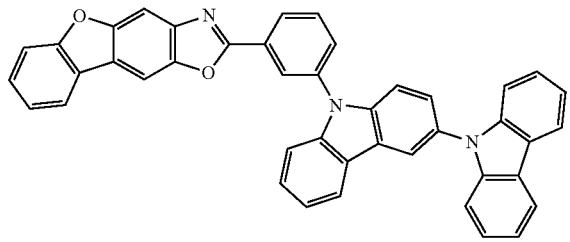

54

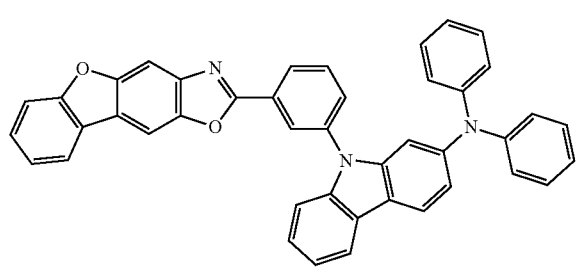

55

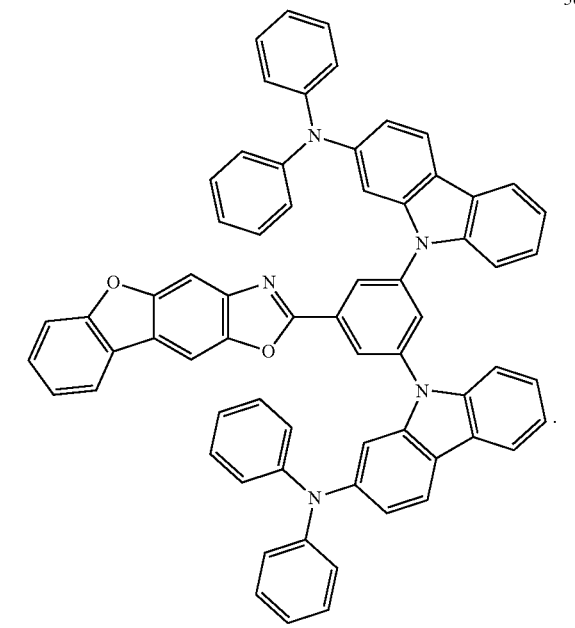

56

9. A compound represented by Formula 1:

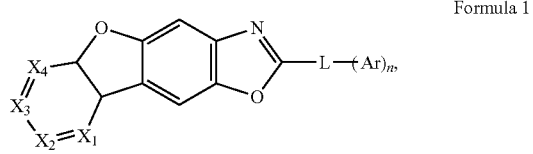

Formula 1 in Formula 1, $X_1$ to $X_4$ are each independently $CR_a$,

L is a substituted or unsubstituted arylene group of 6 to 30 carbon atoms for forming a ring, or a substituted or unsubstituted heteroarylene group of 2 to 30 carbon atoms for forming a ring, "n" is 1 or 2, Ar is a substituted or unsubstituted aryl group of 6 to 15 carbon atoms for forming a ring, or represented by Formula 2:

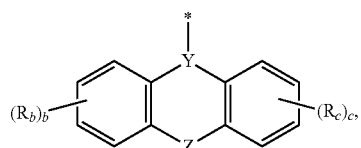

Formula 2 in Formula 2,

Y is N or B,

Z is a direct linkage, O, S, $NR_d$, or $CR_eR_f$,

"b" and "c" are each independently an integer of 0 to 4, and $R_b$ to $R_f$ are each independently a hydrogen atom, a deuterium atom, a halogen atom, a cyano group, a substituted or unsubstituted silyl group, a substituted or unsubstituted amine group, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, and/or combined with an adjacent group to form a ring, and $R_a$ is a hydrogen atom, a deuterium atom, a halogen atom, a cyano group, a substituted or unsubstituted silyl group, a substituted or unsubstituted amine group, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, and/or combined with an adjacent group to form a ring.

10. The compound of claim 9, wherein Formula 1 is represented by Formula 1-1:

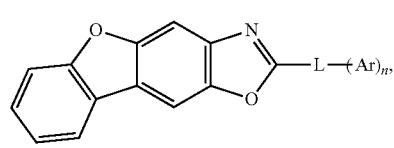

Formula 1-1 in Formula 1-1, L, "n", and Ar are the same as defined in Formula 1.

11. The compound of claim 9, wherein Formula 2 is represented by Formula 2-1 or Formula 2-2:

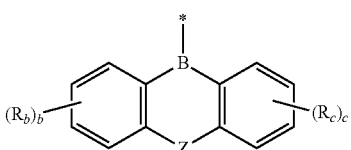

Formula 2-1

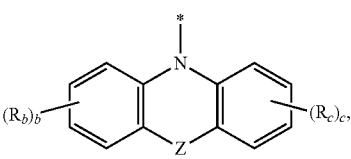

Formula 2-2 in Formula 2-1 and Formula 2-2, Z, $R_b$, $R_c$, "b", and "c" are the same as defined in Formula 2.

12. The compound of claim 11, wherein Formula 2-2 is represented by any one selected from among Formula 2-2A to Formula 2-2E:

Formula 2-2A
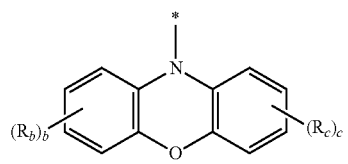

Formula 2-2B
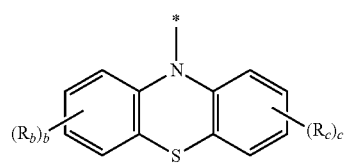

Formula 2-2C
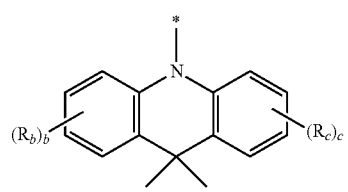

Formula 2-2D
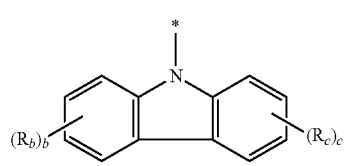

Formula 2-2E
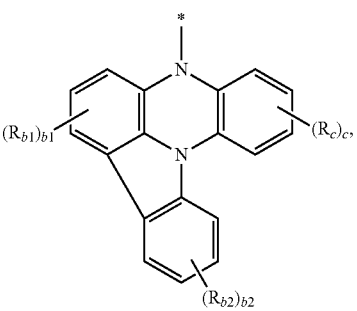

in Formula 2-2E,

"b1" is an integer of 0 to 3, "b2" is an integer of 0 to 4, and $R_{b1}$ and $R_{b2}$ are each independently a hydrogen atom, a deuterium atom, a halogen atom, a cyano group, a substituted or unsubstituted silyl group, a substituted or unsubstituted amine group, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, and/or combined with an adjacent group to form a ring, and in Formula 2-2A to Formula 2-2E, $R_b$, $R_c$, "b", and "c" are the same as defined in Formula 2.

13. The compound of claim 9, wherein the compound represented by Formula 1 is a green dopant to emit green light having a central wavelength of about 500 nm to about 550 nm.

14. The compound of claim 9, wherein the compound represented by Formula 1 is a blue dopant to emit blue light having a central wavelength of about 420 nm to about 470 nm.

15. The compound of claim 9, wherein the compound represented by Formula 1 has an absolute value ($\Delta E_{ST}$) of a difference between a lowest excitation singlet energy level (S1) and a lowest excitation triplet energy level (T1) of about 0.2 eV or less.

16. The compound of claim 9, wherein the compound represented by Formula 1 is represented by any one selected from among compounds in Compound Group 1:

Compound Group 1